(12) United States Patent
McNiven et al.

(10) Patent No.: US 10,661,052 B2
(45) Date of Patent: May 26, 2020

(54) INTRAVASCULAR DEVICE DELIVERY SHEATH

(71) Applicant: Cephea Valve Technologies, Inc., Santa Clara, CA (US)

(72) Inventors: Sean A. McNiven, Menlo Park, CA (US); Randolf von Oepen, Aptos, CA (US); Yongjin Xie, Cupertino, CA (US); Francisco Valencia, East Palo Alto, CA (US); Ken C. Salvador, Hayward, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 160 days.

(21) Appl. No.: 15/662,008

(22) Filed: Jul. 27, 2017

(65) Prior Publication Data

US 2018/0126119 A1    May 10, 2018

Related U.S. Application Data

(60) Provisional application No. 62/368,683, filed on Jul. 29, 2016, provisional application No. 62/430,143, filed on Dec. 5, 2016.

(51) Int. Cl.
*A61M 25/00* (2006.01)
*A61F 2/966* (2013.01)
(Continued)

(52) U.S. Cl.
CPC ........... *A61M 25/005* (2013.01); *A61F 2/966* (2013.01); *A61M 25/0045* (2013.01);
(Continued)

(58) Field of Classification Search
CPC .................................................. A61M 25/005
See application file for complete search history.

(56) References Cited

U.S. PATENT DOCUMENTS

| 4,406,656 A | 9/1983 | Hattler et al. |
| 4,728,319 A | 3/1988 | Masch |

(Continued)

FOREIGN PATENT DOCUMENTS

| CN | 1469724 | 1/2004 |
| CN | 102770080 | 11/2012 |

(Continued)

OTHER PUBLICATIONS

U.S. Appl. No. 15/662,001, Jun. 20, 2019, Office Action.
(Continued)

*Primary Examiner* — Laura A Bouchelle
(74) *Attorney, Agent, or Firm* — Workman Nydegger

(57) ABSTRACT

An intravascular delivery system includes a delivery sheath capable of transmitting a predetermined tension or compression force in a longitudinal direction while maintaining flexibility to navigate tortuous anatomy. A method of delivering a medical device includes inserting an intravascular device delivery system including a delivery sheath having a continuous spine into a bodily lumen. A distal longitudinal force is applied to the delivery sheath. The distal force is transmitted through the continuous spine and across one or more slit cuts of the delivery sheath. A proximal longitudinal force is applied to the delivery sheath. The proximal longitudinal force is transmitted through the continuous spine of the delivery sheath.

17 Claims, 9 Drawing Sheets

(51) Int. Cl.
*A61M 25/06* (2006.01)
*A61M 25/01* (2006.01)
*A61M 25/09* (2006.01)
*A61F 2/24* (2006.01)

(52) U.S. Cl.
CPC .... *A61M 25/0136* (2013.01); *A61M 25/0662* (2013.01); *A61M 25/09* (2013.01); *A61F 2/2436* (2013.01); *A61F 2210/0076* (2013.01); *A61F 2230/0091* (2013.01); *A61F 2250/0018* (2013.01); *A61F 2250/0065* (2013.01); *A61M 25/0051* (2013.01); *A61M 25/0147* (2013.01); *A61M 2025/0046* (2013.01); *A61M 2025/0063* (2013.01); *A61M 2025/0175* (2013.01); *A61M 2025/0681* (2013.01)

(56) References Cited

U.S. PATENT DOCUMENTS

| | | | |
|---|---|---|---|
| 5,053,043 A | 10/1991 | Gottesman et al. | |
| 5,059,213 A | 10/1991 | Chesterfield et al. | |
| 5,078,722 A | 1/1992 | Stevens | |
| 5,236,450 A | 8/1993 | Scott | |
| 5,325,845 A | 7/1994 | Adair | |
| 5,345,945 A | 9/1994 | Hodgson et al. | |
| 5,387,219 A | 2/1995 | Rappe | |
| 5,415,664 A | 5/1995 | Pinchuk | |
| 5,472,423 A | 12/1995 | Gronauer | |
| 5,571,085 A | 11/1996 | Accisano, III | |
| 5,662,606 A | 9/1997 | Cimino et al. | |
| 5,669,919 A | 9/1997 | Sanders et al. | |
| 5,769,812 A | 6/1998 | Stevens et al. | |
| 5,807,405 A | 9/1998 | Vanney et al. | |
| 5,820,591 A | 10/1998 | Thompson et al. | |
| 5,843,103 A | 12/1998 | Wulfman | |
| 5,855,601 A | 1/1999 | Bessler et al. | |
| 5,873,882 A | 2/1999 | Straub et al. | |
| 5,902,334 A | 5/1999 | Dwyer et al. | |
| 5,906,642 A | 5/1999 | Caudillo et al. | |
| 5,957,973 A | 9/1999 | Quiachon et al. | |
| 6,090,118 A | 7/2000 | McGuckin, Jr. | |
| 6,180,059 B1 | 1/2001 | Divino, Jr. et al. | |
| 6,228,110 B1 | 5/2001 | Munsinger | |
| 6,458,137 B1 | 10/2002 | Klint | |
| 6,517,550 B1 | 2/2003 | Konya et al. | |
| 6,695,836 B1 | 2/2004 | DeMello et al. | |
| 6,926,725 B2 | 8/2005 | Cooke et al. | |
| 7,172,617 B2 | 2/2007 | Colgan et al. | |
| 7,344,553 B2 | 3/2008 | Opolski et al. | |
| 7,666,204 B2 | 2/2010 | Thornton et al. | |
| 7,736,388 B2 | 6/2010 | Goldfarb et al. | |
| 7,837,727 B2 | 11/2010 | Goetz et al. | |
| 7,988,724 B2 | 8/2011 | Salahieh et al. | |
| 7,993,303 B2 | 8/2011 | Von Oepen et al. | |
| 8,157,852 B2 | 4/2012 | Bloom et al. | |
| 8,523,881 B2 | 9/2013 | Cabiri et al. | |
| 8,647,323 B2* | 2/2014 | Guo | A61M 25/0012 264/241 |
| 8,911,455 B2 | 12/2014 | Quadri et al. | |
| 8,926,588 B2 | 1/2015 | Berthiaume et al. | |
| 8,926,692 B2 | 1/2015 | Dwork | |
| 9,339,378 B2 | 5/2016 | Quadri et al. | |
| 9,370,423 B2 | 6/2016 | Ryan | |
| 9,393,112 B2 | 7/2016 | Tuval et al. | |
| 9,399,112 B2 | 7/2016 | Shevgoor et al. | |
| 9,668,859 B2 | 6/2017 | Kheradvar et al. | |
| 9,687,373 B2 | 6/2017 | Vad | |
| 9,693,862 B2 | 7/2017 | Campbell et al. | |
| 9,801,745 B2 | 10/2017 | Wubbeling et al. | |
| 10,111,671 B2 | 10/2018 | Bodewadt | |
| 10,376,673 B2 | 8/2019 | Van Hoven et al. | |
| 10,398,553 B2 | 9/2019 | Kizuka | |
| 2001/0002445 A1 | 5/2001 | Vesely | |
| 2002/0013547 A1 | 1/2002 | Paskar | |
| 2004/0049207 A1 | 3/2004 | Goldfarb et al. | |
| 2004/0116848 A1 | 6/2004 | Gardeski et al. | |
| 2004/0127849 A1 | 7/2004 | Kantor | |
| 2004/0133232 A1 | 7/2004 | Rosenbluth et al. | |
| 2004/0147826 A1 | 7/2004 | Peterson | |
| 2005/0038383 A1 | 2/2005 | Kelley et al. | |
| 2005/0085903 A1 | 4/2005 | Lau | |
| 2005/0137695 A1 | 6/2005 | Salahieh et al. | |
| 2005/0256452 A1 | 11/2005 | DeMarchi et al. | |
| 2005/0283231 A1 | 11/2005 | Haug et al. | |
| 2005/0277874 A1 | 12/2005 | Selkee | |
| 2005/0277876 A1 | 12/2005 | Hayden | |
| 2006/0135961 A1 | 6/2006 | Rosenman et al. | |
| 2007/0060997 A1 | 3/2007 | de Boer | |
| 2007/0156225 A1 | 7/2007 | George et al. | |
| 2007/0173757 A1 | 7/2007 | Levine et al. | |
| 2007/0197858 A1 | 8/2007 | Goldfarb et al. | |
| 2007/0203561 A1 | 8/2007 | Forster et al. | |
| 2007/0260225 A1 | 11/2007 | Sakakine et al. | |
| 2007/0299424 A1* | 12/2007 | Cumming | A61M 25/0012 604/527 |
| 2008/0103585 A1 | 5/2008 | Monstadt et al. | |
| 2008/0188850 A1 | 8/2008 | Mody et al. | |
| 2008/0195126 A1 | 8/2008 | Solem | |
| 2009/0036768 A1 | 2/2009 | Seehusen et al. | |
| 2009/0099554 A1 | 4/2009 | Forster et al. | |
| 2009/0163934 A1 | 6/2009 | Raschdorf, Jr. et al. | |
| 2009/0204005 A1 | 8/2009 | Keast et al. | |
| 2009/0240326 A1 | 9/2009 | Wilson et al. | |
| 2009/0276039 A1 | 11/2009 | Meretei | |
| 2009/0281619 A1 | 11/2009 | Le et al. | |
| 2010/0004739 A1 | 1/2010 | Vesely | |
| 2010/0044410 A1 | 2/2010 | Argentine et al. | |
| 2010/0217261 A1 | 8/2010 | Watson | |
| 2010/0249894 A1 | 9/2010 | Oba et al. | |
| 2010/0331776 A1 | 12/2010 | Salahieh et al. | |
| 2011/0112630 A1 | 5/2011 | Groothuis et al. | |
| 2011/0166566 A1 | 7/2011 | Gabriel | |
| 2011/0257718 A1 | 10/2011 | Argentine | |
| 2011/0307049 A1 | 12/2011 | Kao | |
| 2012/0022640 A1 | 1/2012 | Gross et al. | |
| 2012/0065464 A1 | 3/2012 | Elllis et al. | |
| 2012/0109078 A1* | 5/2012 | Schaeffer | A61M 25/0012 604/264 |
| 2012/0172915 A1 | 7/2012 | Fifer et al. | |
| 2012/0316639 A1 | 12/2012 | Kleinschrodt | |
| 2012/0330348 A1 | 12/2012 | Strauss et al. | |
| 2012/0330408 A1 | 12/2012 | Hillukka et al. | |
| 2013/0041314 A1 | 2/2013 | Dillon | |
| 2013/0066342 A1 | 3/2013 | Dell et al. | |
| 2013/0103001 A1 | 4/2013 | BenMaamer et al. | |
| 2013/0131775 A1 | 5/2013 | Hadley | |
| 2014/0107693 A1 | 4/2014 | Plassman | |
| 2014/0148889 A1 | 5/2014 | Deshmukh et al. | |
| 2014/0180124 A1 | 6/2014 | Whiseant et al. | |
| 2014/0228871 A1 | 8/2014 | Cohen et al. | |
| 2014/0276966 A1 | 9/2014 | Ranucci et al. | |
| 2014/0324164 A1 | 10/2014 | Gross et al. | |
| 2015/0005704 A1 | 1/2015 | Heisel et al. | |
| 2015/0005801 A1* | 1/2015 | Marquis | A61M 25/0097 606/194 |
| 2015/0088189 A1 | 3/2015 | Paul, Jr. | |
| 2015/0112430 A1 | 4/2015 | Creaven et al. | |
| 2015/0272759 A1 | 10/2015 | Argentine | |
| 2015/0306806 A1 | 10/2015 | Dando et al. | |
| 2016/0045311 A1 | 2/2016 | McCann et al. | |
| 2017/0035566 A1 | 2/2017 | Krone et al. | |
| 2017/0042678 A1 | 2/2017 | Ganesan et al. | |
| 2017/0080186 A1* | 3/2017 | Salahieh | A61M 25/0053 |
| 2017/0232238 A1 | 8/2017 | Biller et al. | |
| 2018/0028177 A1 | 2/2018 | von Oepen et al. | |
| 2018/0028215 A1 | 2/2018 | Cohen | |
| 2018/0028305 A1 | 2/2018 | von Oepen et al. | |
| 2018/0028779 A1 | 2/2018 | von Oepen et al. | |
| 2018/0055636 A1 | 3/2018 | Valencia et al. | |
| 2018/0055637 A1 | 3/2018 | von Oepen et al. | |
| 2018/0056033 A1 | 3/2018 | von Oepen et al. | |
| 2018/0056043 A1 | 3/2018 | von Oepen et al. | |
| 2018/0092744 A1 | 4/2018 | von Oepen et al. | |

(56) References Cited

U.S. PATENT DOCUMENTS

| | | |
|---|---|---|
| 2018/0133454 A1 | 5/2018 | von Oepen et al. |
| 2018/0360457 A1 | 12/2018 | Ellis et al. |
| 2019/0030285 A1 | 1/2019 | Prabhu et al. |
| 2019/0274831 A1 | 9/2019 | Prabhu |

FOREIGN PATENT DOCUMENTS

| | | |
|---|---|---|
| CN | 103841899 | 6/2014 |
| EP | 1980288 | 10/2008 |
| EP | 2537487 | 12/2012 |
| EP | 2702965 | 3/2014 |
| EP | 3009103 | 4/2016 |
| JP | 2003062072 | 3/2003 |
| JP | 2006528911 | 12/2006 |
| JP | 2013516244 | 5/2013 |
| WO | WO 2001051114 | 7/2001 |
| WO | WO 2007044285 | 4/2007 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | WO 2012020521 | 2/2012 |
| WO | WO 2012151396 | 11/2012 |
| WO | WO 2014064694 | 5/2014 |
| WO | WO 2014121280 | 8/2014 |
| WO | WO 2014128705 | 8/2014 |
| WO | WO 2015191938 | 12/2015 |
| WO | WO 2016022797 | 2/2016 |
| WO | WO 2016112085 | 7/2016 |
| WO | WO 2016144708 | 9/2016 |
| WO | WO 2016150806 | 9/2016 |
| WO | WO 2016183526 | 11/2016 |
| WO | WO 2018023038 | 2/2018 |
| WO | WO 2018023045 | 2/2018 |
| WO | WO 2018044446 | 3/2018 |
| WO | WO 2018044447 | 3/2018 |
| WO | WO 2018044448 | 3/2018 |
| WO | WO 2018044449 | 3/2018 |
| WO | WO 2018067788 | 4/2018 |
| WO | WO 2018093426 | 5/2018 |

OTHER PUBLICATIONS

U.S. Appl. No. 15/662,001, Oct. 4, 2019, Office Action.
U.S. Appl. No. 15/662,001, Dec. 18, 2019, Notice of Allowance.
U.S. Appl. No. 15/662,013, Dec. 5, 2019, Advisory Action.
U.S. Appl. No. 15/662,066, Jul. 11, 2019, Office Action.
U.S. Appl. No. 15/662,066, Dec. 16, 2019, Office Action.
U.S. Appl. No. 15/662,142, Dec. 20, 2019, Advisory Action.
U.S. Appl. No. 15/662,076, Oct. 8, 2019, Notice of Allowance.
U.S. Appl. No. 15/662,089, Oct. 7, 2019, Office Action.
U.S. Appl. No. 15/662,089, Jan. 10, 2020, Office Action.
U.S. Appl. No. 15/662,093, Mar. 7, 2019, Office Action.
U.S. Appl. No. 15/662,093, Aug. 29, 2019, Office Action.
U.S. Appl. No. 15/662,093, Dec. 3, 2019, Office Action.
U.S. Appl. No. 15/662,014, May 31, 2019, Office Action.
U.S. Appl. No. 15/662,014, Oct. 2, 2019, Notice of Allowance.
U.S. Appl. No. 15/662,098, Jul. 5, 2019, Office Action.
U.S. Appl. No. 15/724,499, Jul. 15, 2019, Notice of Allowance.
U.S. Appl. No. 15/724,499, Aug. 27, 2019, Notice of Allowance.
U.S. Appl. No. 15/724,499, Nov. 22, 2019, Notice of Allowance.
Takizawa H et al: "Development of a microfine active bending catheter equipped with MIF tactile sensors", Micro Electro Mechanical Systems, 1999. MEMS '99. Twelfth IEEE International Conference on Orlando, FL, USA Jan. 17-21, 1999, Piscataway, NJ, USA,IEEE, US, Jan. 17, 1999 (Jan. 17, 1999), pp. 412-417, XP010321677, ISBN: 978-0-7803-5194-3 figures 1-3.

\* cited by examiner

INTRAVASCULAR DEVICE DELIVERY SHEATH

CROSS-REFERENCE TO RELATED APPLICATIONS

This application claims priority to and the benefit of: U.S. Patent Application Ser. No. 62/368,683, filed Jul. 29, 2016, entitled "Intravascular Device Delivery Sheath", and U.S. Patent Application Ser. No. 62/430,143, filed Dec. 5, 2016, entitled "Intravascular Device Delivery Sheath", the disclosures of which are incorporated herein by this reference in their entireties.

BACKGROUND OF THE DISCLOSURE

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. Intravascular procedures can also enable faster recovery times with lower associated costs and risks of complication.

An example of an intravascular procedure that significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more deflecting mechanisms, which can be achieved by tension cable, or other mechanisms positioned inside the catheter. Precise control of the distal end of the catheter allows for more reliable and faster positioning of a medical device and/or implant and other improvements in the procedures.

An intravascularly delivered device needs to be placed precisely to ensure a correct positioning of the medical device, which is essential for its functionality, as the device may be difficult to reposition after the device is fully deployed from the delivery system. Additionally, the ability to recapture a partially deployed device is desirable in the event that the distal end of the catheter moves relative to the target location and compromises the precise positioning of the device.

The expansion and/or recapture of the device requires the collapse of one or more movable portions of the device. The one or more movable portions expand and/or collapse toward the longitudinal axis of a sheath during longitudinal movement of the sheath over the transverse exterior of the device. Proximal movement of the sheath relative to the device allows the device to expand beyond a diameter of the sheath. Distal movement of the sheath relative to the device constrains the device in the tip of the sheath. More rigid and/or robust devices with a high outwards force require a stiffer sheath and/or greater longitudinal forces to move the sheath relative to the device. Increasing the stiffness of the sheath is undesirable during intravascular procedures since a stiff sheath might not be able to be delivered through a tortuous anatomy.

BRIEF SUMMARY OF THE DISCLOSURE

In an embodiment, a hybrid tubular member includes an inner layer and an outer layer. The inner layer has a proximal end and a distal end with a longitudinal axis extending therebetween. The inner layer has an inner layer angle. The outer layer longitudinally overlaps the inner layer and is positioned circumferentially outside of and around the inner layer. The outer layer has an outer layer angle that is less than the inner layer angle.

In another embodiment, an intravascular device delivery system comprises an elongated member including a delivery catheter and a hybrid delivery sheath positioned radially outside and circumferentially about the delivery catheter. The delivery catheter has a proximal end and a distal end with a longitudinal axis extending therebetween. The hybrid delivery sheath includes an inner layer and an outer layer. The inner layer has a proximal end and a distal end with a longitudinal axis extending therebetween. The inner layer has an inner layer angle. The outer layer longitudinally overlaps the inner layer and is positioned circumferentially outside of and around the inner layer. The outer layer has an outer layer angle that is less than the inner layer angle.

In yet another embodiment, a method of delivering a medical device includes inserting an intravascular device delivery system including a hybrid delivery sheath having an inner layer and an outer layer into a bodily lumen. The method further includes then applying a distal longitudinal force to the hybrid deliver sheath and moving one of the inner layer of the hybrid delivery sheath and the outer layer of the hybrid delivery sheath relative to the other. The method also includes transmitting the distal force through the inner layer of the hybrid delivery sheath and applying a proximal longitudinal force to the hybrid delivery sheath. Further, the method includes moving one of the outer layer of the hybrid delivery sheath and the inner layer of the hybrid delivery sheath relative to the other and transmitting the proximal longitudinal force through an outer layer of the hybrid delivery sheath.

In still yet another embodiment, an intravascular device delivery system includes an elongated element having a longitudinal axis along a length thereof. The elongated element has a body with an outer surface and an inner surface. The body has a continuous spine extending in a direction along or around the longitudinal axis and a plurality of cuts from the outer surface to the inner surface.

In another embodiment, an intravascular device delivery system includes an elongated member that includes a delivery catheter and a delivery sheath. The delivery catheter has a proximal end, a distal end, and a longitudinal axis extending therebetween. The delivery sheath is positioned radially outside and circumferentially about the delivery catheter and coaxial with the delivery catheter. The delivery sheath includes a body with an outer surface and an inner surface and a longitudinal axis extending along a length thereof. The body has a continuous spine extending in a direction of the longitudinal axis and a plurality of cuts from the outer surface to the inner surface.

In a further embodiment, a method of delivering a medical device includes inserting an intravascular device delivery system including a delivery sheath having a continuous spine into a bodily lumen. The method also includes applying a distal longitudinal force to the delivery sheath and transmitting the distal force through the continuous spine and across one or more slit cuts of the delivery sheath. The method further includes applying a proximal longitudinal force to the delivery sheath and transmitting the proximal longitudinal force through the continuous spine of the delivery sheath.

Still yet a further embodiment includes a hybrid tubular member having an inner layer, an outer layer, and one or more tensioning elements. The inner layer has a proximal end and a distal end, with a longitudinal axis extending therebetween. The inner layer also includes a coil. The outer layer longitudinally overlaps the inner layer and is positioned circumferentially outside and around the inner layer. The outer layer also includes a coil. The one or more tensioning elements extend from the proximal end of the inner layer to the distal end of the inner layer.

This summary is provided to introduce a selection of concepts that are further described below in the detailed description. This summary is not intended to identify specific features of the claimed subject matter, nor is it intended to be used as an aid in limiting the scope of the claimed subject matter.

Additional features of embodiments of the disclosure will be set forth in the description, which follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof that are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIG. 6-1 is a perspective view of a portion of a braided sleeve according to on embodiment of the present disclosure;

FIG. 6-2 is a perspective view of a coil according to an embodiment of the present disclosure;

FIG. 6-3 is a cross sectional view of a delivery sheath according to the present disclosure disposed about a deflected inner catheter;

FIG. 7-1 is a perspective cutaway view of another embodiment of a delivery sheath, according to the present disclosure;

FIG. 7-2 is a side view of the embodiment of a delivery sheath of FIG. 7-1, according to the present disclosure;

FIG. 11-1 is a schematic representation of the embodiment of the delivery sheath of FIG. 10 laid flat, according to the present disclosure;

FIG. 11-2 is a schematic representation of another embodiment of a delivery sheath laid flat, according to the present disclosure;

DETAILED DESCRIPTION

Figure 1:
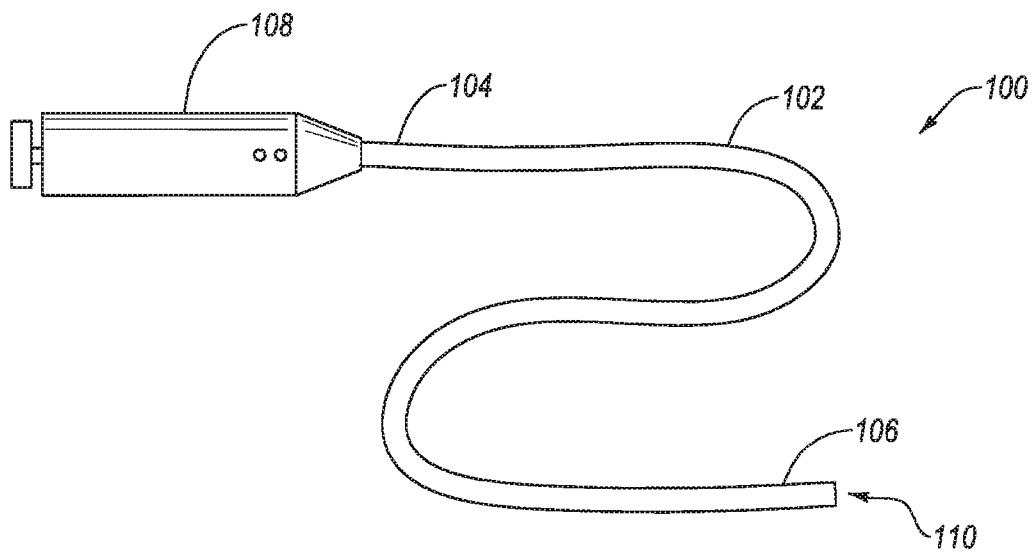
FIG. 1 is a schematic representation of an embodiment of an intravascular device delivery system, according to the present disclosure.

One or more specific embodiments of the present disclosure will be described below. In an effort to provide a concise description of these embodiments, some features of an actual embodiment may or may not be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to manufacturing and using intravascular device delivery systems or other steerable intravascular systems. An intravascular device delivery system may allow a medical professional to deliver an intravascular or other medical device to a target location in a patient's body. While the present disclosure will describe intravascular device delivery systems and applications thereof in relation to intravascular procedures in the heart, it should be understood that the devices, systems, and methods described herein may be applicable to other bodily lumens and/or cavities. Additionally, elements described in relation to any embodiment depicted and/or described herein may be combinable with elements described in relation to any other embodiment depicted and/or described herein. For example, any element described in relation to an embodiment depicted in FIG. 4 may be combinable with any element of an embodiment described in FIG. 16, and any element described in relation to an embodiment described in FIG. 9 may be combinable with any element of an embodiment depicted in FIG. 14.

An intravascular device delivery system may include a flexible elongated member that has a distal end and a proximal end. One or more handles may be connected to a proximal end of the elongated member to allow a user, such as a medical professional and/or clinician, to control one or more movements of the elongated member. An intravascular device may be positioned at and/or connected to the distal end of the elongated member.

In some embodiments, the elongated member may include a plurality of elements. For example, the elongated member may include a plurality of elements that extend from the proximal end to the distal end. In some embodiments, at least one of the elements of the elongated member may be located radially within a delivery sheath of the elongated member. In at least one embodiment, at least one element of the elongated member is located coaxially within a delivery sheath.

In some embodiments, the handle(s) may include one or more controls (e.g., a knob, a button, a lever, or other controls) that may move at least one part of the intravascular device delivery system relative to another. For example, the handle(s) may include one or more controls for moving a delivery sheath of the elongated member relative to a delivery catheter or other element of the elongated member. The handle(s) may move the delivery sheath relative to another element of the elongated member in a proximal direction, in a distal direction, in a rotational direction, or combinations thereof.

FIG. 1 illustrates a schematic representation of an intravascular device delivery system 100. The system 100 may include an elongated member 102 having a proximal end 104 and a distal end 106. A handle 108 may be connected to the proximal end 104 of the elongated member 102. An intravascular device 110 may be positioned at, disposed within, and/or connected to the distal end 106 and constrained by the elongated member 102.

The elongated member 102 may be flexible in parts and stiffer in other parts, allowing the elongated member 102 to traverse a patient's tortuous vasculature or other anatomy. In some embodiments, the elongated member 102 may deliver the intravascular device 110 to a target location in the patient's body, such as delivering a replacement heart valve to the heart. In other embodiments, the system 100 and elongated member 102 may be provided without an intravascular device 110 at the distal end 106 such that the system may recapture, reposition, or otherwise move an intravascular device previously positioned in the patient's body. Furthermore the system 100 might be used to perform other functions as for example being used as a positioning system to have a separate element crossing the septum wall between the right and the left atrium of a patient's heart.

The elongated member 102 of the system 100 may include one or more elements therein. An element of the elongated member 102 may include one or more deflecting catheters, elements to provide torque control, catheters or elements connecting a therapeutic device to the catheter or to the handle(s) 108, a guidewire, a guidewire lumen, lateral movable or fixed sheath, other tubular and/or solid element, or combinations thereof. In some embodiments, an element of the elongated member 102 may extend an entire length of the elongated member 102 from the proximal end 104 to the distal end 106 of the elongated member 102. In other embodiments, an element of the elongated member 102 may have a length less than the entire length of the elongated member. For example, an element may provide support to the elongated member 102 from the proximal end 104 toward the distal end 106 without continuing the entire length to the distal end 106.

Figure 2:
FIG. 2 is a side cutaway detail of the elongated member of the embodiment of an intravascular device delivery system of FIG. 1, according to the present disclosure.

FIG. 2 is a side cutaway view of an embodiment of an elongated member 102 having a plurality of elements positioned concentrically within one another. For example, an elongated member 102 may have delivery sheath 112 with one or more elements positioned radially within the delivery sheath 112. In some embodiments, the delivery sheath 112 may be an outermost element of the elongated member 102. In other embodiments, at least part of the delivery sheath 112 may be within an outermost element of the elongated member 102.

In some embodiments, an elongated member 102 may have a delivery catheter 114 positioned radially within the delivery sheath 112. For example, at least a portion of the delivery catheter 114 may longitudinally overlap with a portion of the delivery sheath 112 and the delivery catheter 114 may be within a lumen or other cavity of the delivery sheath 112. In other embodiments, the delivery sheath 112 may have a plurality of elements positioned radially within the delivery sheath 112. For example, the delivery catheter 114 and an inner catheter 116 may be positioned radially within the delivery sheath 112. For example, both the delivery catheter 114 and inner catheter 116 may be positioned radially within the delivery sheath 112 and radially adjacent one another. In another example, the inner catheter 116 may be radially within the delivery catheter 114 and both may be radially within the delivery sheath 112. In yet other embodiments, the delivery sheath 112 may have the delivery catheter 114, the inner catheter 116, and a guidewire 118 radially within the delivery sheath 112, as shown in FIG. 2.

In some embodiments, the delivery sheath 112 and the delivery catheter 114 may be coaxial with one another. For example, the delivery sheath 112 and delivery catheter 114 may share a longitudinal axis 126 therethrough. In other embodiments, the delivery sheath 112, delivery catheter 114, inner catheter 116, guidewire 118, or combinations thereof may be coaxial and/or share the longitudinal axis 126 of the elongated member 102.

In some embodiments, at least one of the delivery sheath 112, delivery catheter 114, inner catheter 116, and guidewire 118 may be a steerable element. For example, at least one of the delivery sheath 112, delivery catheter 114, inner catheter 116, and guidewire 118 may have a plurality of wires, cables, threaded, sutures, or chambers that may allow a lateral force to be applied to the element, as known in the art, to allow steerability of the elongated member 102. In at least one embodiment, the delivery catheter 114 may be a steerable catheter.

In at least one embodiment, a friction-reducing layer and/or coating may be located between the delivery sheath 112 and the delivery catheter 114. In other embodiments, a friction-reducing layer and/or coating may be located on the delivery sheath 112 and/or delivery catheter 114 to reduce friction between the delivery sheath 112 and the delivery catheter 114. For example, a friction-reducing layer and/or coating may include a polytetraflouroethylene (PTFE) layer positioned between or on one or both of the delivery sheath 112 and the delivery catheter 114. In other examples, other lubricious coatings, such as perfluoroalkoxy (PFA), fluorinated ethylene propylene, other flouropolymer, ceramic coatings, one or more materials combined with a polymer structure (such as PROPELL available from FOSTER CO.), other materials, or combinations thereof, may be applied between the elements of the elongated member 102 to reduce friction between the elements during movement relative to one another. In yet other examples, a hydrophilic or hydrophobic layer may be positioned between and/or on the delivery sheath 112 and the delivery catheter 114.

Figure 3:
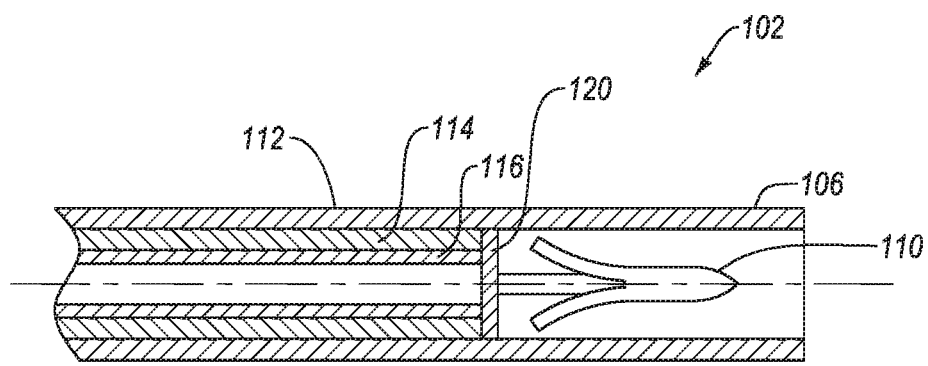
FIG. 3 is a side cross-sectional view of the distal end of the elongated member of the embodiment of an intravascular device delivery system of FIG. 1, according to the present disclosure.

FIG. 3 is a side cross-sectional view of an embodiment of the distal end 106 of the elongated member 102 described in relation to FIG. 2. In some embodiments, the distal end 106 may have an intravascular device 110 positioned therein and/or connected thereto. For example, the intravascular device 110 may be longitudinally adjacent to a distal end cap 120. The distal end cap 120 may be longitudinally fixed to the delivery catheter 114 and/or the inner catheter 116. In some embodiments, the intravascular device 110 may be removably connected to the distal end cap 120. For example, the distal end cap 120 may have one or more retention features (e.g., threaded, pins, grooves, resilient clips, etc.) thereon and the intravascular device 110 may have one or more complimentary retention features thereon, such that the intravascular device 110 may selectively engage with the distal end cap 120. In other embodiments, the intravascular device 110 may abut the distal end cap 120 without interlocking, adhering, or otherwise connecting to the distal end cap 120.

The distal end 106 may have a delivery sheath 112 at least partially longitudinally overlapping the intravascular device 110. In some embodiments, the intravascular device 110 may be moveable between a contracted state and an expanded state. For example, a MITRACLIP valve repair device may have a plurality of moveable members that may be deployed radially away from a body of the device and beyond a width of the delivery sheath 112.

In other embodiments, the intravascular device 110 may be a self-expanding intravascular device 110 with a contracted state and an expanded state. For example, the intravascular device 110 may be biased toward the expanded state such that the delivery sheath 112 holds the intravascular device 110 in the contracted state, and removal of the delivery sheath 112 (e.g., moving the delivery sheath 112 in a proximal direction) from a longitudinally overlapping position, such as shown in FIG. 3, may allow the expansion of the intravascular device 110 toward an expanded state. In some embodiments, the intravascular device 110 may include a shape memory material ("SMM") such as a shape memory polymer and/or a shape-memory metal. For example, the intravascular device 110 may include or be made of a nickel titanium alloy.

Figure 4:
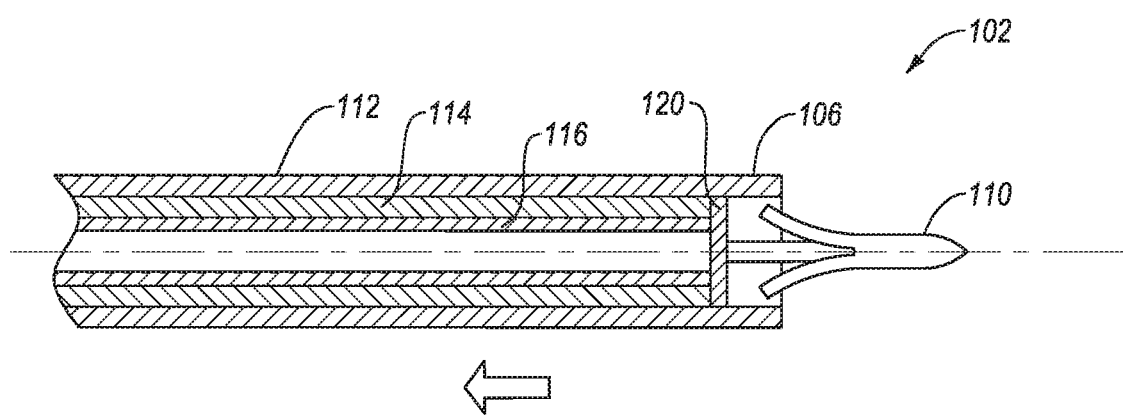
FIG. 4 is a side cross-sectional view of the embodiment of the distal end of FIG. 3 with the delivery sheath retracted, according to the present disclosure.

The intravascular device 110 in a contracted state may apply an expansive force to the delivery sheath 112. The force experienced between the intravascular device 110 and the delivery sheath 112 may create and/or increase a frictional force the delivery sheath 112 and the intravascular device 110 and/or the delivery catheter 114. In some embodiments, the frictional force while moving the delivery sheath 112 relative to the intravascular device 110 and/or the delivery catheter 114 may be greater than 2 pounds (8.9 Newton), greater than 10 pounds (44.5 Newtons), greater than 20 pounds (89.0 Newtons), greater than 30 pounds (133.4 Newtons), greater than 40 pounds (177.9 Newtons), or greater than 50 pounds (222.4 Newtons). As shown in FIG. 4, a proximal force greater than the frictional force may be necessary to move the delivery sheath 112 in a proximal direction relative to the intravascular device 110 and/or the delivery catheter 114.

The intravascular device 110 may expand radially outward beyond the delivery sheath 112 after proximal or distal movement of the delivery sheath 112 relative to the intravascular device 110. The delivery sheath 112 may move in a proximal or distal direction relative to the delivery catheter 114, inner catheter 116, distal end cap 120, or combinations thereof. The distal end cap 120 may limit and/or prevent the proximal movement of the intravascular device 110 during proximal movement of the delivery sheath 112.

Figure 5:
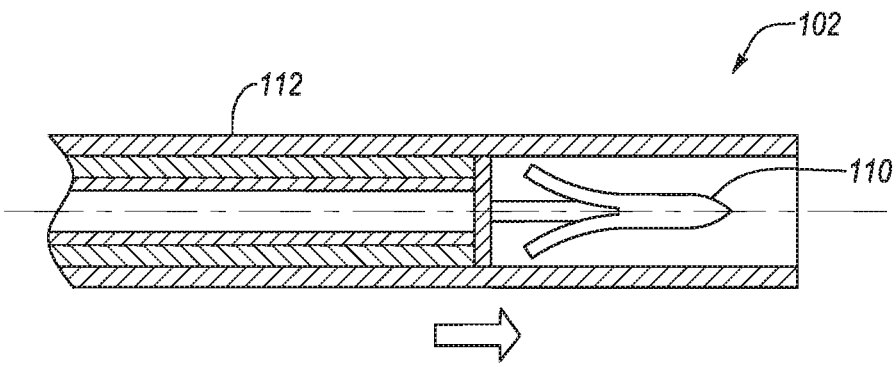
FIG. 5 is a side cross-sectional view of the embodiment of the distal end of FIG. 4 with the delivery sheath advanced, according to the present disclosure.

In embodiments with one or more retention features on the distal end cap 120 and/or the intravascular device 110, the longitudinal and/or rotational position of the intravascular device 110 relative to the distal end cap 120 may be fixed. For example, after a partial expansion of the intravascular device 110, the intravascular device 110 may be urged back to a contracted state upon distal movement of the delivery sheath 112 relative to the intravascular device 110 as shown in FIG. 5. FIG. 5 illustrates the recapture of the intravascular device 110 for repositioning or, if necessary, for removal from the patient's body. In some embodiments, movement of the delivery sheath 112 may require collapsing the intravascular device 110 to a contracted state, such as closing the clips of a MITRACLIP valve repair device. In other embodiments, such as a self-expanding intravascular device 110, movement of the delivery sheath 112 in a distal or proximal direction relative to the intravascular device 110 may apply a compressive force to the intravascular device 110 to contain the intravascular device 110 in the contracted state.

To be able to apply significant forces, as for example 40 pounds (177.9 Newton), at the distal end of the catheter to un-sheath or re-sheath a medical device, conventional catheter constructions might not be adequate. Typical braided thin walled catheters will collapse when a high compression force is applied and will lengthen or break under a high tensile force and/or change an inner or outer diameter. As an example, a braided delivery sheath 112 may lengthen during high-tension forces and reduce in inner and/or outer diameter. Therefore, the delivery sheath 112 might interlock with the more inner elements (e.g., delivery catheter 114, inner catheter 116, guidewire 118) of the elongated member 102, which will increase the force to move or prevent movement of the delivery sheath 112 relative to the more inner elements of the elongated member 102.

A typical staged coil construction might be able to withstand high compression forces but has very little resistance against tension. Conventional spiral coil sleeves may lengthen in a longitudinal direction upon application of tension forces during an application of the proximal force on the delivery sheath 112 and fail to adequately transmit tension force from the proximal end of the elongate member to the distal end of the elongate member. For example, application of 40 pounds (177.9 Newtons) at a proximal end may stretch a conventional spiral coil without transmission of tension force to the distal end. Similarly, a conventional braided sleeve may shorten in a longitudinal direction upon application of a distal force to the proximal end of the braided sleeve and fail to adequately transmit compression force from the proximal end of the elongate member to the distal end of the elongate member. For example, application of 40 pounds (177.9 Newtons) at the proximal end may compress a conventional braided sleeve without transmission of the compression force to the distal end.

In some embodiments, a hybrid delivery sheath, such as embodiments described in relation to FIG. 6 through FIG. 9, may transmit both compression and tension forces applied at a proximal end of the delivery sheath to the distal end of the delivery sheath without substantial change to the longitudinal length of the delivery sheath. In other embodiments, a hybrid delivery sheath may transmit tension force applied at a proximal end of the delivery sheath to the distal end of the delivery sheath without substantial change to the longitudinal length of the delivery sheath. For example, a hybrid delivery sheath may transmit tension force without substantial change to the longitudinal length of the delivery sheath and may foreshorten by 5%, 10%, 15%, 20%, 25%, 30%, 40%, 50%, 75%, 100%, 150%, 200%, 250%, 300%, 350%, 400% or any value therebetween during compression. In at least one embodiment, a coil may compress by a percentage of the initial longitudinal length of the delivery sheath before the coils contact one another and the coil transmits compression forces along the longitudinal length thereof. For example, the inner layer may be a coil with an initial spacing of between 0.1 mm and 5.0 mm, between 1 mm and 4 mm, between 2 mm to 3 mm, or any values therebetween to provide a bending radius to navigate the anatomy of a patient's heart.

Figure 6:
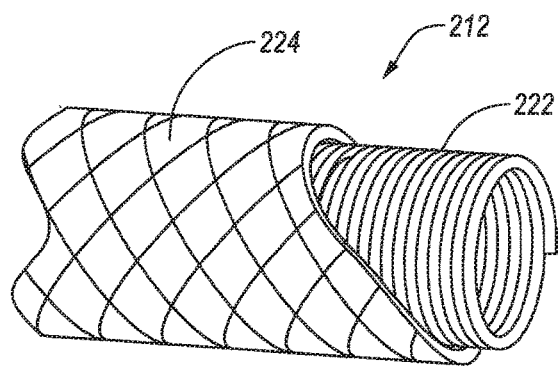
FIG. 6 is a perspective cutaway view of an embodiment of a delivery sheath, according to the present disclosure.
Figures 1, 6:
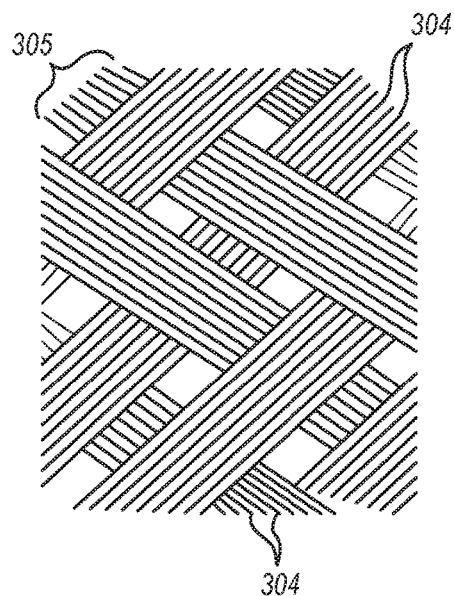
Figures 2, 6:
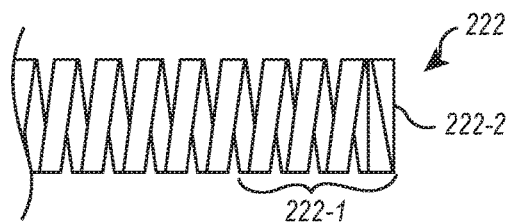
Figures 3, 6:
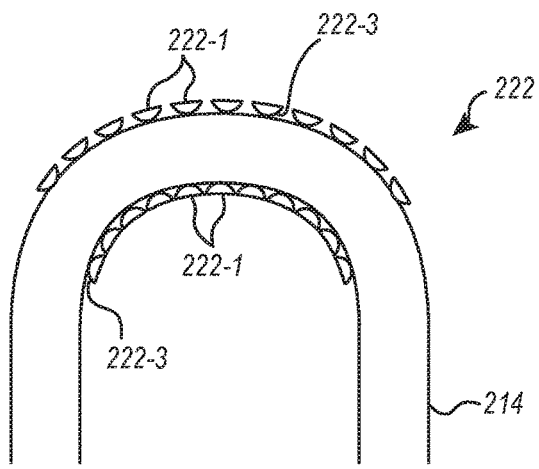

FIG. 6 is a perspective cutaway view of a hybrid delivery sheath 212. The delivery sheath 212 may have an inner layer 222 and an outer layer 224. In some embodiments, the inner layer 222 may be a spiral coil that is made of or includes a resilient coil material. For example, the coil material may be stainless steel, nickel titanium (e.g., Nitinol), other metal alloy, a thermoplastic, other polymers such as PEEK, ceramics, carbon tubing, glass, or combinations thereof. In at least one embodiment, the coil may be a stainless steel coil that has a droop value of 5:1 or higher. In some embodiments, the droop value may be 11:1. The inner layer 222 may be sized relative to the outer layer 224 such that the inner layer 222 has an outer diameter ("OD") in a relaxed state that is substantially the same as an inner diameter ("ID") of the outer layer 224 in a relaxed state. In other embodiments, the inner layer 222 may be sized relative to the outer layer 224 such that the inner layer 222 has an OD in a relaxed state that is less than the ID of the outer layer 224 in a relaxed state. In yet other embodiments, the inner layer 222 may be sized relative to the outer layer 224 such that the inner layer 222 has an OD that is greater than the ID of the outer layer 224 in a relaxed state. In such embodiments, the outer layer 224 may apply a radially compressive force to the inner layer 222 at rest, without external forces applied to the delivery sheath 212.

In some embodiments, the outer layer 224 may be a braided sleeve. For example, a braided sleeve may include a plurality of threads or fibers that are woven together. For example, a braided sleeve may include a plurality of threads that extend at an angle to one another and are woven together in a repeating pattern. The plurality of threads may be woven in a diamond two wire two-under-two, over-two pattern; a half-load single wire over-one, one-under pattern; a full-load single wire over-two, under-two pattern; other alternating woven patterns; or combinations thereof. In other embodiments, a braided sleeve may include a single thread routed substantially straight longitudinally through the plurality of threads.

The threads may be round threads, elliptical threads, or flat threads. The threads may be made of or include a variety of reinforcement materials, such as, metals, metal alloys, thermoplastics, other polymers, ceramics, glasses or combinations thereof. In some embodiments, the reinforcement material or materials may have a greater elastic modulus than the body material. For example, a braided sleeve may include a mixture of threads with different properties, such as stainless steel threads woven with polymer threads. In at least one embodiment, a braided sleeve may include a plurality of 304 stainless steel wires woven in a diamond pattern as illustrated in FIG. 6-1. Such an embodiment of a braided sleeve may include between 16 and 72 threads of stainless steel. For example, a braided sleeve may include 24 strands 305, with each strand consisting of between two and 10 wires. For instance, as shown in FIG. 6-1, each strand 305 includes eight wires 304 arranged parallel to one another.

The inner layer 222 and the outer layer 224 may be longitudinally fixed to one another at or near a proximal end of the delivery sheath 212 and the distal end of the delivery sheath 212. In some embodiments, the outer layer 224 may be welded or soldered to the inner layer 222 at a proximal end and a distal end of the delivery sheath 212. In other embodiments, the outer layer 224 may be fixed to the inner layer 222 with an adhesive at a proximal end and a distal end of the delivery sheath 212. In yet other embodiments, the outer layer 224 may be fixed to the inner layer 222 via an intermediate element (e.g., an annular end cap) at a proximal end and a distal end of the delivery sheath 212. In yet other embodiments, the outer layer 224 and the inner layer 222 may be longitudinally fixed relative to one another at one or more points between a proximal end and a distal end of the delivery sheath. For example, the outer layer 224 and the inner layer 222 may be longitudinally fixed relative to one another at a centerpoint. In other embodiments, the delivery sheath 212 may extend longitudinally along a portion of the elongated member. The delivery sheath may be welded, soldered, or otherwise connected to another elongated member that extends proximally from the delivery sheath 212 or distally from the delivery sheath 212. For example, a proximal end of the delivery sheath 212 may be welded to a distal end of a hypotube to transmit forces to the delivery sheath 212 from the proximal end of the elongated member. In at least one embodiment, the hypotube may be between approximately 25 millimeters and 1 meter in longitudinal length or any length therebetween, and the delivery sheath 212 may be between approximately 50 millimeters 300 millimeters or any length therebetween in longitudinal length. In some embodiments, the delivery sheath 212 may be approximately 150 millimeters in longitudinal length.

In some embodiments, the inner layer 222 may be connected directly or indirectly (e.g., via a stainless steel ring) to a hypotube. For instance, a proximal end of the inner layer 222 may be welded to a hypotube or associated ring. To facilitate a secure connection between the inner layer 222 and the hypotube (or associated ring), the proximal end of the inner layer 222 may have a closed configuration as shown in FIG. 6-2. For instance, the coils elements 222-1 adjacent the end of the inner layer 222 may be positioned closer together. Additionally, the wire or other material forming the coil may taper close the end of the inner layer 222 such that an end surface of the inner layer 222 is substantially orthogonal to the longitudinal axis of the inner layer 222. For instance, the coil element 222-2 may taper so that a cross-sectional dimension thereof that extends parallel to a longitudinal axis of the inner layer 222 progressively decreases as the coil element 222-2 approaches the end of the inner layer 222. The distal end of the inner layer 222 may have a closed configuration similar to that illustrated in FIG. 6-2.

In some embodiments where the inner layer 222 includes or is a spiral coil, the wire or other material that forms the spiral coil may have a cross section shape that reduces friction and/or facilitates relative movement between the inner layer and a delivery catheter disclosed therein. For instance, FIG. 6-3 illustrates a spiral coil 222 disposed about a delivery catheter 214. As shown, the spiral coil 222 and the delivery catheter 214 are deflected (forming a bend). When so deflected, the space between individual coil elements 222-1 on the outside of the bend increases and the space between individual coil elements 222-1 on the inside of the bend decreases. The individual coil elements 222-1 can have a semi-circular cross sectional shape with the rounded surface 222-3 being oriented toward the interior of the spiral coil 222. The rounded interior surfaces 222-3 of the individual coil elements 222-1 allows for the spiral coil 222 to deflect as shown in FIG. 6-3 while still presenting a relatively smooth surface, devoid of sharp corners, towards the delivery catheter 214. The relatively smooth surface provided by the rounded surfaces 222-3 allows for relative movement between the spiral coil 222 and the delivery catheter 214 with minimal, if any, interference between relatively sharp corners on the spiral coil 222 and the delivery catheter 214.

Figures 1, 7:
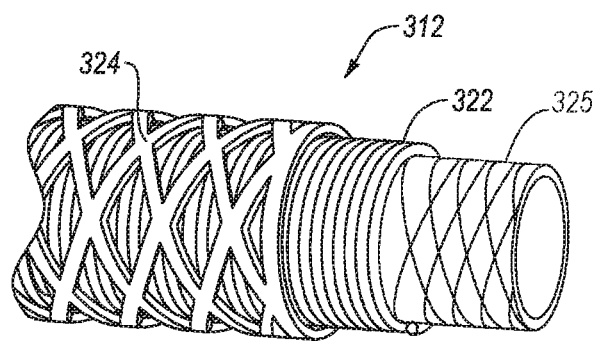
Figures 2, 7:
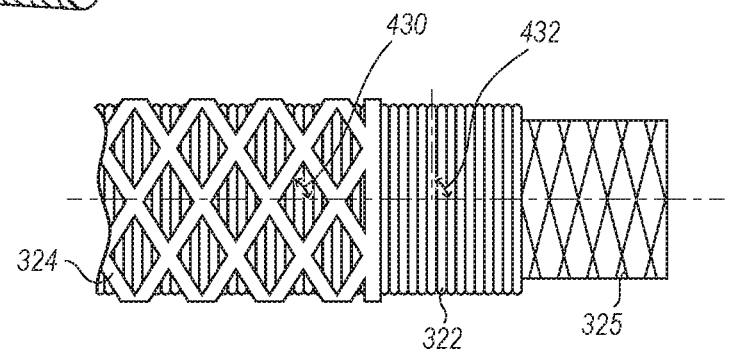

In other embodiments, a hybrid delivery sheath 312 may include a hypotube with one or more cuts therein, such as shown in FIGS. 7-1 and 7-2. In some embodiments, the outer layer 324 may be a cut hypotube including nitinol, stainless steel, or other resilient biocompatible material. For example, a hypotube may be laser-cut, hydrojet cut, mechanically cut (e.g., cut by a die), cut by any other suitable technique, or combinations thereof. In some embodiments, a cut hypotube may be a stent or a similar structure. The hypotube may have a plurality of openings cut through a body of the material to allow expansion and/or contraction of the hypotube in a transverse direction. The inner layer 322 may be a coil and/or a braided sleeve, as described herein. In other embodiments, the inner layer 322 may be a cut hypotube and the outer layer 324 may be a coil and/or a braided sleeve, as described herein.

In embodiments having an inner layer comprising a coil (as described in relation to FIG. 6) or a cut hypotube or stent (as described in relation to FIGS. 7-1 and 7-2), an inner surface of the inner layer may introduce ridges, ledges, lips, edges, or other topography that may inhibit the movement of an element or device along the inner surface of the hybrid delivery sheath. In at least one embodiment, such as that shown in FIGS. 7-1 and 7-2 a hybrid delivery sheath may include a braided contact layer 325 in addition to the inner layer 322 and outer layer 324 as described herein. The braided contact layer 325 may provide a more continuous inner surface and limit mechanical impedances to the movement of an element or device along the inner surface of the hybrid delivery sheath 312. In some embodiments, the contact layer may not be braided. For instance, the contact layer may be formed of a continuous material and/or have a smooth surface.

Figure 8:
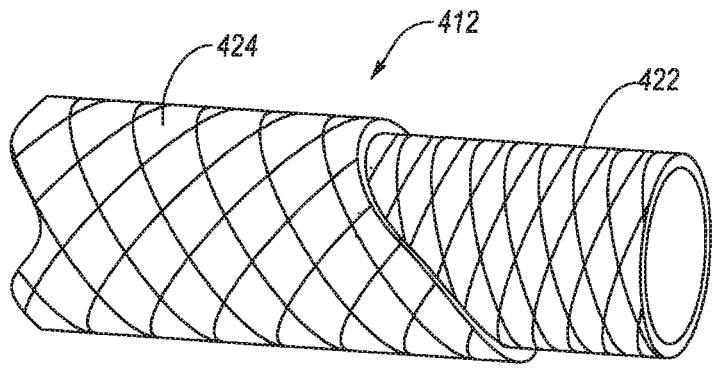
FIG. 8 is a perspective cutaway view of yet another embodiment of a delivery sheath, according to the present disclosure.

Referring now to FIG. 8, in yet other embodiments, a delivery sheath 412 has an inner layer 422 and an outer layer 424 that are similar in construction. For example, FIG. 8 illustrates an embodiment of a delivery sheath 412 in which each of the inner layer 422 and the outer layer 424 comprises a braided sleeve. In other examples, some embodiments of a delivery sheath may have an inner layer and an outer layer that are each cut hypotubes. In yet other examples, some embodiments of a delivery sheath may have an inner layer and an outer layer that are each coils. The inner layer 422 and the outer layer 424 may have differing orientations of the constituent elements (e.g., the wires, fibers, struts, coils, or other elements) that form the inner layer 422 and outer layer 424, respectively.

Figure 9:
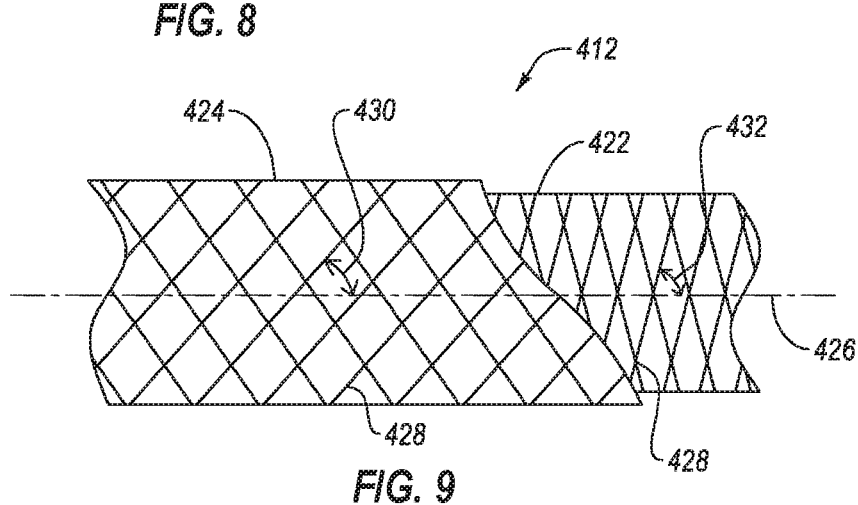
FIG. 9 is a side cutaway view of the embodiment of the delivery sheath of FIG. 8, according to the present disclosure.

In the embodiment depicted in FIG. 9, the inner layer 422 of the delivery sheath 412 and the outer layer 424 of the delivery sheath 412 may each be made of a plurality of wires 428 braided to form a braided sleeve. The wires 428 of the outer layer 424 may be oriented at an outer layer angle 430 relative to a longitudinal axis 426 of the delivery sheath 412. The wires 428 of the inner layer 422 may be oriented at an inner layer angle 432 relative to the longitudinal axis 426 of the delivery sheath 412. In some embodiments, the outer layer angle 430 may be less than the inner layer angle 432. The inner layer angle 432 and the outer layer angle 430 (i.e., inner layer angle 432 to outer layer angle 430) may define a layer angle ratio in a range having upper and lower values including any of 1.1, 1.2, 1.3, 1.4, 1.5, 1.6, 1.7, 1.8, 1.9, 2.0, 2.2, 2.4, 2.6, 2.8, 3.0, 3.5, 4.0, 5.0, or any value therebetween. For example, the layer angle ratio may be in a range of 1.1 to 5.0 (e.g., when the outer layer angle 430 is 15°, the inner layer angle 432 may be between 16.5° and 75°). In other examples, the layer angle ratio may be in a range of 1.2 to 4.0 (e.g., when the outer layer angle 430 is 20°, the inner layer angle 432 may be between 24° and 80°). In yet other examples, the layer angle ratio may be in a range of 1.3 to 3.0 (e.g., when the outer layer angle 430 is 25°, the inner layer angle 432 may be between 32.5° and 75°). In at least one example, the outer layer angle 430 may be 45° and the inner layer angle 432 may be 85°.

In other embodiments, such as a coil (as described in relation to FIGS. 6, 7-1, and 7-2) or a cut hypotube or stent (as described in relation to FIGS. 7-1 and 7-2), the inner layer angle 432 and/or the outer layer angle 430 may be defined by the angle of the coil or of the stent support members relative to the longitudinal axis 426. For example, an outer layer or inner layer including a coil may have an outer layer angle 430 or inner layer angle 432, respectively, which is at least partially related to the pitch of the coil. In other examples, an outer layer or inner layer including a cut hypotube or stent may have an outer layer angle 430 or inner layer angle 432, respectively, which is the angle of the stent support members relative to the longitudinal axis 426.

In some embodiments, the inner layer 422 may provide the delivery sheath 412 strength under compression and the outer layer 424 may provide the delivery sheath 412 strength in tension. For example, the inner layer angle 432 being greater than the outer layer angle 430 may allow the inner layer 422 to expand in a direction transverse to the longitudinal axis 426 less than the outer layer 424 during compression applied to a proximal end of the delivery sheath 412. (The inner layer 422 and outer layer 424 may be longitudinally fixed relative to one another at the proximal and distal ends of the delivery sheath, as described herein.)

In some embodiments, the inner layer 422 may have an inner layer angle 432 close to 90° relative to the longitudinal axis 426 such that the inner layer 422 transmits compression force along the longitudinal axis 426 similarly to a solid delivery sheath. In some examples, the inner layer angle 432 may be greater than 75°. In other examples, the inner layer angle 432 may be greater than 80°. In yet other examples, the inner layer angle 432 may be greater than 85°.

In another example, the inner layer angle 432 being greater than the outer layer angle 430 may allow the outer layer 424 to contract in a direction transverse to the longitudinal axis 426 more than the inner layer 422 during tension applied to a proximal end of the delivery sheath 412. (The inner layer 422 and outer layer 424 may be longitudinally fixed relative to one another at the proximal and distal ends of the delivery sheath, as described herein.)

In some embodiments, the outer layer 424 may contract more than the inner layer 422 in tension, and the outer layer 424 may apply a compressive force to the inner layer 422. The inner layer 422 may then support the outer layer 424, limiting and/or preventing the further contraction of the outer layer 424 toward the inner layer 422 (e.g., the outer layer 424 may "cinch down" on the inner layer 422), allowing a tension force to be applied to the outer layer 424 of the delivery sheath 412 without substantial radial contraction of the outer layer 424 and/or delivery sheath 412.

In some embodiments, the delivery sheath 412 may contract transversely to the longitudinal axis 426 less than 25% of a transverse dimension of the delivery sheath 412 during application of a predetermined tension force (e.g., 40 pounds (177.9 Newtons)). In other embodiments, the delivery sheath 412 may contract transversely to the longitudinal axis 426 less than 20% of a transverse dimension of the delivery sheath 412 during application of a predetermined tension force. In yet other embodiments, the delivery sheath 412 may contract transversely to the longitudinal axis 426 less than 15% of a transverse dimension of the delivery sheath 412 during application of a predetermined tension force. In further embodiments, the delivery sheath 412 may contract transversely to the longitudinal axis 426 less than 10% of a transverse dimension of the delivery sheath 412 during application of a predetermined tension force. In yet further embodiments, the delivery sheath 412 may contract transversely to the longitudinal axis 426 less than 5% of a transverse dimension of the delivery sheath 412 during application of a predetermined tension force. In still further other embodiments, the delivery sheath 412 may contract transversely to the longitudinal axis 426 less than 2% of a transverse dimension of the delivery sheath 412 during application of a predetermined tension force.

Figure 10:
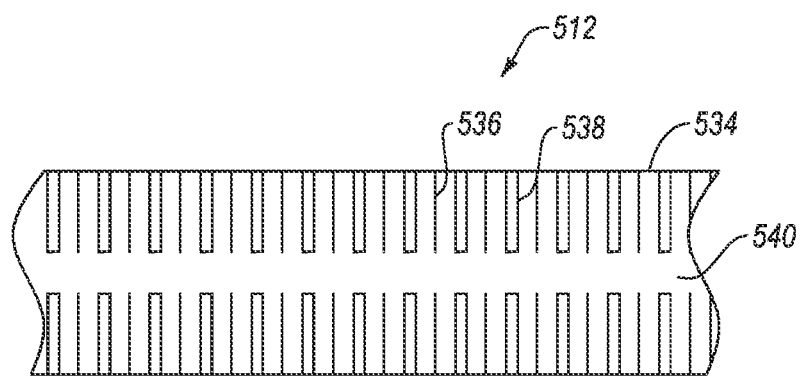
FIG. 10 is a side view of a further embodiment of a delivery sheath, according to the present disclosure.

FIG. 10 is a side view of another embodiment of a delivery sheath 512, according to the present disclosure. In some embodiments, the delivery sheath 512 may include a body, such as tubular element 534, that has a plurality of slits 536 and/or island cuts 538 therein that define at least one longitudinally continuous spine 540. A longitudinally continuous spine 540 may be a portion of the tubular element 534 that is continuous and uninterrupted along a longitudinal length of the tubular element 534 at a fixed angular location on the tubular element 534. For example, a longitudinally continuous spine 540 may extend from a proximal end of the delivery sheath 512 to a distal end of the delivery sheath 512 at a fixed angular location on the tubular element 534 without a cut (e.g., a slit 536 or an island cut 538) interrupting the spine 540. In some embodiments, at least a portion of an island cut 538 at a first longitudinal position may be rotationally aligned with at least a portion of a slit 536 at a second longitudinal position.

It should be understood that while embodiments of a pattern of cuts is described in relation to the delivery sheath 512, the embodiments of a pattern of cuts described may be used with other elements of an elongated member, including delivery catheters, inner catheter, tubular guidewires, and other elongated elements.

In some embodiments, the longitudinally continuous spine 540 may allow the delivery sheath 512 to transmit tension force applied at a proximal end of the delivery sheath 512 to a distal end of the delivery sheath 512 without substantial elongation of the delivery sheath 512. In other embodiments, the longitudinally continuous spine 540 may allow the delivery sheath 512 to transmit compression force applied at a proximal end of the delivery sheath 512 to a distal end of the delivery sheath 512 without substantial shortening of the delivery sheath 512. For example, some embodiments of a delivery sheath 512 according to the present disclosure may exhibit a change in a longitudinal length of the delivery sheath 512 of less than 10% during application of either or both a predetermined compression force (e.g., of 40 pounds (177.9 Newtons)) and a predetermined tension force (e.g., of 40 pounds (177.9 Newtons)). In other examples, some embodiments of a delivery sheath 512 according to the present disclosure may exhibit a change in a longitudinal length of the delivery sheath 512 of less than 5% during application of either or both a predetermined compression force and a predetermined tension force. In yet other examples, some embodiments of a delivery sheath 512 according to the present disclosure may exhibit a change in a longitudinal length of the delivery sheath 512 of less than 2% during application of either or both a predetermined compression force and a predetermined tension force.

Figures 1, 11:
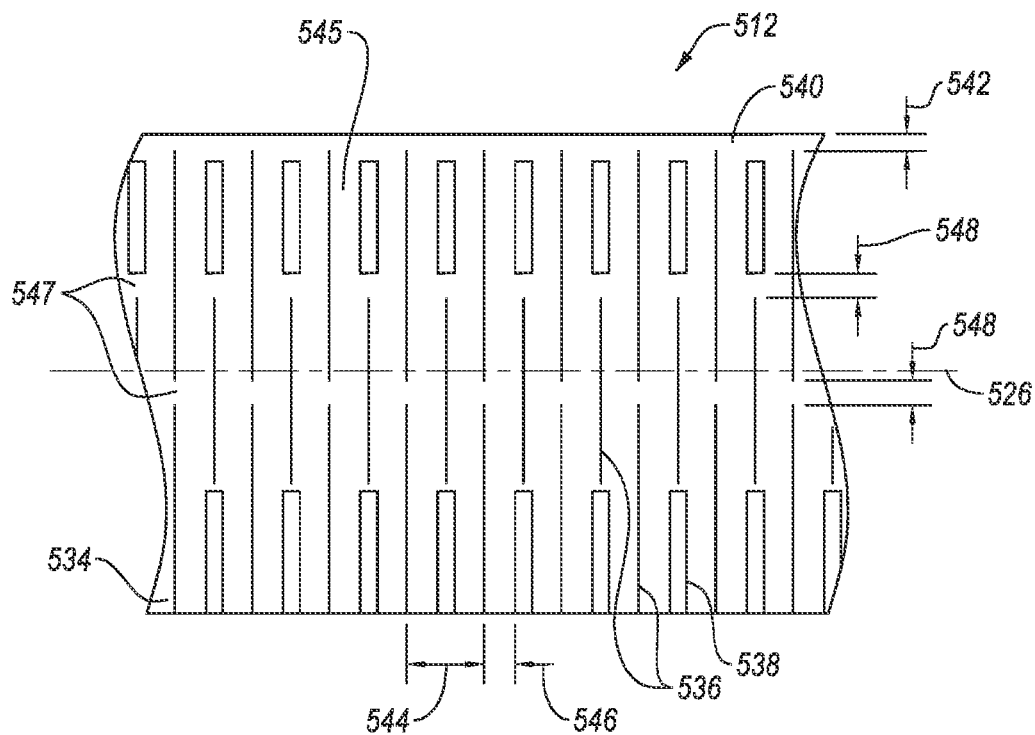
Figures 2, 11:
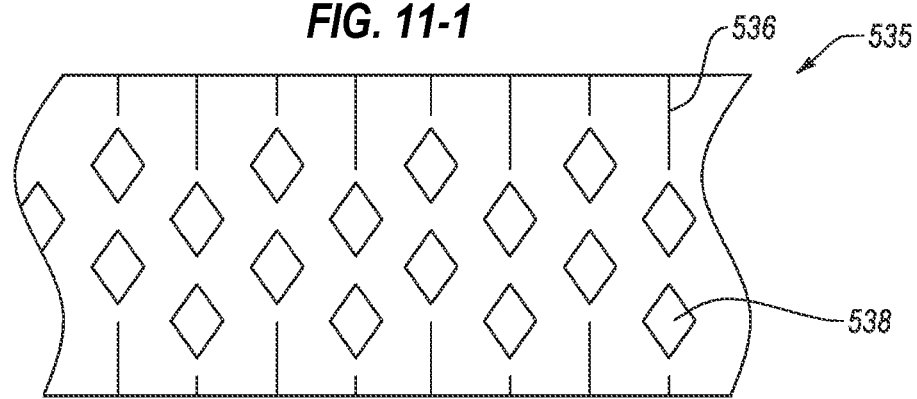

FIG. 11-1 illustrates the tubular element 534 and pattern of slits 536 and island cuts 538 of FIG. 10 laid in a flat view. One should interpret FIG. 11-1 to connect the lower edge of FIG. 11-1 to the upper edge of FIG. 11-1 to form a circumferentially continuous tubular element 534 as shown in FIG. 10.

In FIG. 11-1, the longitudinally continuous spine 540 is oriented parallel to the longitudinal axis 526 of the delivery sheath 512. The spine 540 may have a spine width 542 that is at least partially related to an outer circumference of the tubular element 534 (i.e., the height of the flat view shown in FIG. 11-1). The spine width 542 may have a spine width percentage relative to the circumference of the outer circumference in range having an upper value, a lower value, or upper and lower values including any of 0.40%, 0.45%, 0.50%, 0.55%, 0.60%, 0.65%, 0.70%, 0.75%, 0.80%, 0.85%, 0.90%, 0.95%, 1.00%, 1.10%, 1.20%, 1.30%, 1.40%, 1.50%, 1.60%, 1.70%, 1.80%, 1.90%, 2.00%, or any values therebetween. For example, the spine width percentage may be in a range of 0.40% to 2.00%. In other examples, the spine width percentage may be in a range of 0.50% to 1.80%. In yet other examples, the spine width percentage may be in a range of 0.60% to 1.00%. In at least one example, the spine width percentage may be 0.64% of the circumference of the tubular element 534.

In some embodiments, the delivery sheath 512 may have a plurality of rings 545. In other embodiments, the delivery sheath 512 may have a plurality of ring sets 544 that form a repeating pattern of slits 536 and/or island cuts 538. The ring sets 544 may have a ring length 546 between each longitudinal set of slits 536 and island cuts 538. In some embodiments, a ring set 544 may have a plurality of rings 545 each with a different ring length 546. In other embodiments, a ring set 544 may have a single ring length 546 such that each longitudinal set of slits 536 and/or island cuts 538 may be equally longitudinally spaced by a ring length 546. A slit 536 may be a single cut, such as a laser cut, hydrojet cut, mechanical cut, or other cut through the tubular element 534 with little or no thickness transverse to the direction of the slit 536. For example, a slit 536 may be perpendicular to the longitudinal axis 526 of the delivery sheath 512 and have a little or no thickness in the longitudinal direction.

An island cut 538 may be a rectangular, elliptical, polygonal, irregular, other shaped cut that has a thickness transverse to the direction of the island cut 538, such that the island cut 538 defines an area that is void of material in the tubular element 534. In some embodiments, an island cut 538 may have a thickness in a longitudinally direction that is at least partially related to a circumference of the tubular element 534. The island cut 538 may have a thickness in the longitudinal direction that defines an island cut percentage relative to the circumference of the tubular element 534. The island cut percentage may be in a range having upper and lower values including any of 0.20%, 0.25%, 0.30%, 0.35%, 0.40%, 0.45%. For example, the island cut percentage may be between 0.20% and 0.45%. In other examples, the island cut percentage may be between 0.25% and 0.40%. In yet other examples, the island cut percentage may be between 0.30% and 0.35%. In at least one example, the island cut percentage may be 0.32%

The slits 536 may allow for expansion of the tubular element 534 at the location of the slit 536 during lateral deflection of the delivery sheath 512 away from the slit 536, while transmitting compression forces in the longitudinal direction. The island cuts 538 may allow compression of the tubular element 534 at the location of the island cut 538 during lateral deflection of the delivery sheath 512 toward the island cut 538. The links 547 allow transmission of compression and tension forces between rings 545 in the longitudinal direction.

In some embodiments, the ring sets 544 may have a repeating pattern of slits 536 and island cuts 538 with links 547 located angularly between the slits 536, island cuts 538, and the spine 540. In some embodiments, the ring sets 544 may repeat, such that the angular location of slits 536 and/or island cuts 538 may repeat each ring, every other ring, every third ring, every fourth ring, or more. For example, the embodiment of a ring set 544 in FIG. 11-1 depicts a ring having a pair of slits 536 longitudinally aligned and angularly offset by 180° from one another with a link 547 and the spine 540 angularly separating the slits 536. The link 547 may be angularly offset by 180° from the spine 540.

Longitudinally displaced by a ring length 546 from the ring having a pair of slits 536 is a ring having a slit 536 and a pair of island cuts 538. The slit 536 and the pair of island cuts 538 are angularly separated from one another by a link 547 or the spine 540. In some embodiments, the links 547 may be spaced about the circumference of the tubular element 534 at equal intervals with the spine 540 (i.e., 120° in the depicted embodiment). In other embodiments, the links 547 may be spaced in unequal angular intervals with the spine 540.

In an embodiment with two links 547 and the spine 540 in a ring 545, the ring 545 may have a pair of island cuts 538 on either angular side of the spine 540, and a slit 536 angularly opposing the spine 540. Longitudinally displaced by a ring length 546 from the ring having a slit 536 and a pair of island cuts 538 is another ring set 544 that begins with a ring having a pair of slits 536, repeating the pattern in the longitudinal direction.

In some embodiments, a ring length 546 may be at least partially related to the circumference of the tubular element 534. A ring length percentage may be a ratio of the ring length 546 relative to the circumference of the tubular element 534. For example, an embodiment of a tubular element 534 with a 31.4 mm circumference and a 0.3 mm ring length 546 may have a ring length percentage of 0.95%. In some embodiments, the ring length percentage may be in a range having upper and lower values including any of 0.60%, 0.70%, 0.80%, 0.90%, 1.00%, 1.10%, 1.20%, 1.30%, 1.40%, 1.50%, 1.60%, 1.70%, 1.80%, 1.90%, 2.00%, or any values therebetween. For example, the ring length percentage may be between 0.60% and 2.00%. In other examples, the ring length percentage may be between 0.70% and 1.85%. In yet other examples, the ring length percentage may be between 0.80% and 1.70%.

In some embodiments, the links 547 may have a link width 548 that is at least partially related to the circumference of the tubular element 534. For example, a link width percentage may be the ratio of the link width 548 relative to the circumference of the tubular element 534. For example, an embodiment of a tubular element 534 with a 31.4 mm circumference and a 0.5 mm link width 548 may have a link width percentage of 1.59%. In some embodiments, the link width percentage may be in a range having upper and lower values including any of 0.60%, 0.70%, 0.80%, 0.90%, 1.00%, 1.10%, 1.20%, 1.30%, 1.40%, 1.50%, 1.60%, 1.70%, 1.80%, 1.90%, 2.00% or any values therebetween. For example, the ring length percentage may be between 0.60% and 2.00%. In other examples, the ring length percentage may be between 0.80% and 1.90%. In yet other examples, the ring length percentage may be between 1.00% and 1.80%.

In some embodiments, a braided sleeve, cut hypotube, coil, or other element described herein as an outer layer may be used to support a cut tubular element, such as tubular element 534 as described in relation to FIGS. 10 and 11-1 or a similar cut tubular member, via transmission of tension forces. In other embodiments, a tubular element, such as tubular element 534 as described in relation to FIGS. 10 and 11-1 or a similar cut tubular member may be used independently of an outer layer under tension. In particular, a tubular element lacking a continuous spine, such as the cut hypotube shown as the outer layer 324 of FIGS. 7-1 and 7-2, may be assisted by an outer layer that transmits tension force via transmission of tension forces to form a hybrid delivery sheath. For example, FIG. 11-2 illustrates a cut tubular element 535 having a rotationally aligned (i.e., forming a line in the longitudinal direction) series of slits 536 that may allow transmission of compression forces along a length of the tubular element 535, but may not transmit tension forces along the length of the tubular element 535 without longitudinal elongation and/or transverse contraction. The cut tubular element 535 may have a plurality of island cuts 538 to increase flexibility of the cut tubular element 535. While the slits may allow portions of the cut tubular element 535 to abut one another and transmit compression forces, the cut tubular element 535 may elongate longitudinally and/or contract transversely under tension. An outer layer (such as a wire braid) around the cut tubular element 535 or similar, as described herein, may provide transmission of tension forces through the wire braid.

Embodiments of delivery sheaths according to the present disclosure may maintain lateral flexibility to navigate the anatomy of a patient while transmitting predetermined compression and tension forces. In some embodiments, the predetermined compression and tension forces have a magnitude of 20 pounds (88.9 Newtons), 25 pounds (111.2 Newtons), 30 pound (133.4 Newtons), 32 pounds (142.3 Newtons), 35 pounds (155.7 Newtons), 36 pounds (160.1 Newtons), 40 pounds (177.9 Newtons), 45 pounds (200.2 Newtons), 50 pounds (222.4 Newtons), 55 pounds (244.7 Newtons), 60 pounds (266.9 Newtons), 62 pounds (275.8 Newtons), or more. A handle may facilitate application of compression and/or tension forces to the delivery sheath.

Figure 12:
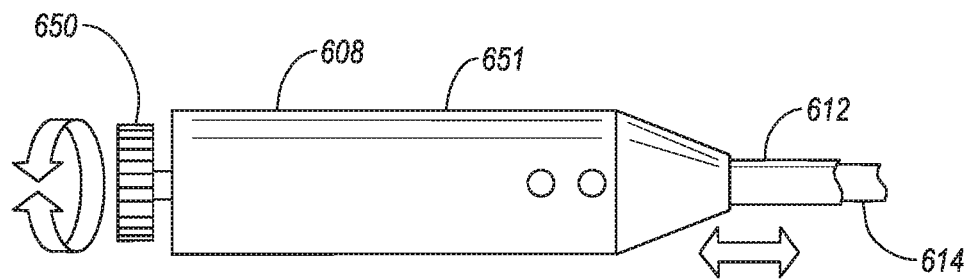
FIG. 12 is a side view of an embodiment of an intravascular device delivery system having a rotatable knob, according to the present disclosure.

FIG. 12 illustrates an embodiment of a handle 608 that may translate a delivery sheath 612 in a longitudinal direction. In some embodiments, the handle 608 may include one or more controls, such as knobs 650 or other rotational controls, which may allow a user to input force relative to the handle body 651. In other embodiments, the knobs 650 may be levers or sliders that allow force transmission to the delivery sheath 612. The rotation of the knob 650 relative to the body 651 may translate the delivery sheath 612 in a longitudinal direction relative to an intravascular device. For example, the intravascular device may be a self-expanding intravascular device, such as described in FIG. 1. The longitudinal movement of the delivery sheath 612 relative to the intravascular device may at least partially deploy the intravascular device.

Figure 13:
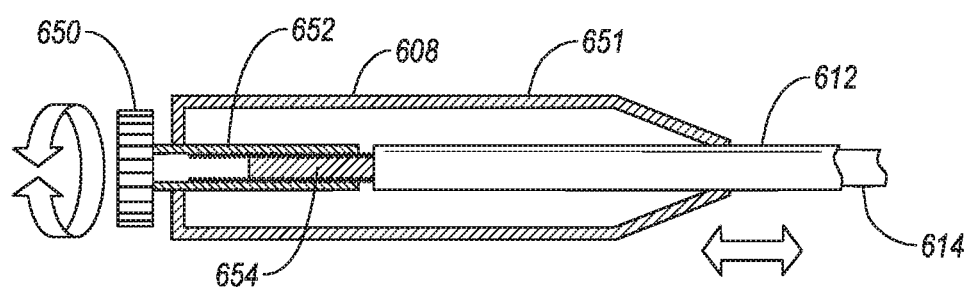
FIG. 13 is a side cross-sectional view of the embodiment of the intravascular device delivery system of FIG. 12, according to the present disclosure.

FIG. 13 is a side cross-sectional view of the embodiment of the handle 608 in FIG. 12. FIG. 13 illustrates the knob 650 being rotational fixed to a first threaded member 652 that may engage with a second threaded member 654 fixed to the delivery sheath 612. In some embodiments, the first threaded member 652 may be located externally to at least part of the second threaded member 654 (e.g., the first threaded member 652 has a threaded inner surface and the second threaded member 654 has a threaded outer surface). In other embodiments, at least part of the first threaded member 652 may be located internally to the second threaded member 654 (e.g., the first threaded member 652 has a threaded outer surface and the second threaded member 654 has a threaded inner surface).

The knob 650 and first threaded member 652 may be longitudinally fixed relative to the handle body 651 (e.g., by one or more bearings) such that rotation of the first threaded member 652 (e.g., via rotation of the knob 650) relative to the second threaded member 654 may translate the second threaded member 654 and the delivery sheath 612 longitudinally relative to the handle 608 to move the intravascular device between an expanded state and a contracted state.

Figure 14:
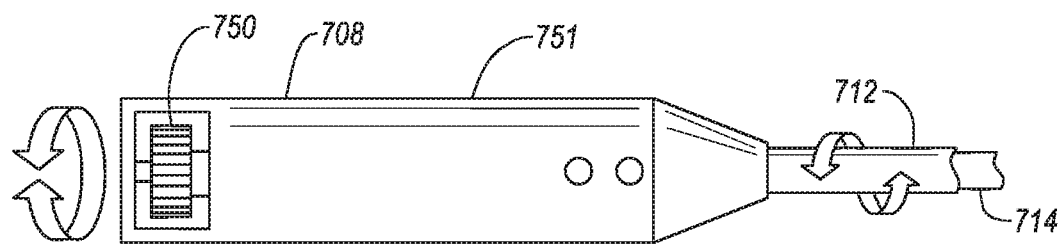
FIG. 14 is a side view of another embodiment of an intravascular device delivery system having a rotatable knob, according to the present disclosure.

FIG. 14 is a side view of another embodiment of a handle 708 according to the present disclosure. The handle 708 may have a knob 750 or other rotational control that may rotate the delivery sheath 712 and translate a delivery sheath 714 in a longitudinal direction relative to the handle body 751. Translating the delivery sheath 712 in a longitudinal direction may move the delivery sheath 712 relative to an intravascular device. In some embodiments, the rotation of the delivery sheath 712 can act to screw the delivery sheath 712 forwards or backwards.

Figure 15:
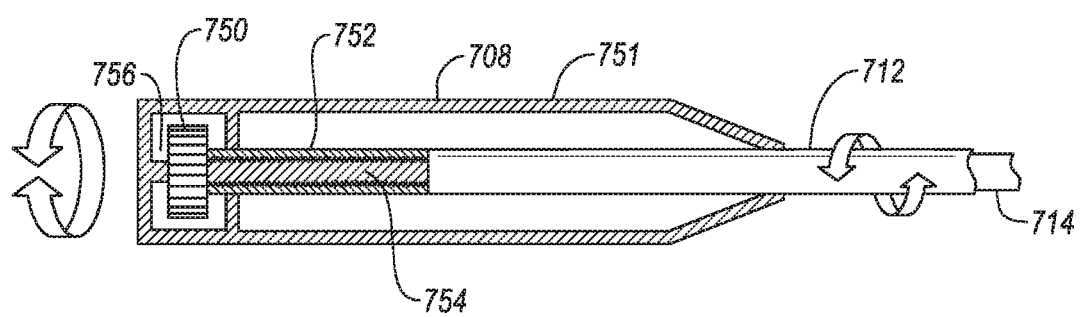
FIG. 15 is a side cross-sectional view of the embodiment of the intravascular device delivery system of FIG. 14, according to the present disclosure.

As shown in FIG. 15, the knob 750 may be rotationally and longitudinally fixed to the delivery sheath 712, either directly or indirectly. In some embodiments, the knob 750 may be fixed directly to the delivery sheath 712. In other embodiments, such as that shown in FIG. 15, the knob 750 may be fixed to a first threaded member 752, which may be fixed to the delivery sheath 712.

The first threaded member 752 may engage with a second threaded member 754 that may be fixed relative to the handle body 751, such as in a knob housing 756 that may limit the longitudinal translation of the knob 750 to a deployment distance of the intravascular device. The rotation of the knob 750 may rotate the first threaded member 752 relative to the second threaded member 754 and translate the first threaded member 752 and knob 750 in a longitudinal direction. The rotation and translation of the first threaded member 752 may be transmitted to the delivery sheath 712 to rotate and translate the delivery sheath 712 relative to the handle 708 and the intravascular device.

In some embodiments, rotation of the delivery sheath 712 may reduce a longitudinal force (i.e., compression and/or tension) necessary to move the delivery sheath 712 relative to one or more elements of an elongated member, such as that described in relation to FIG. 1 through FIG. 5. The rotation of the delivery sheath 712 may reduce stick-slip behaviors by ensuring the delivery sheath 712 exhibits a dynamic friction between the delivery sheath 712 and a contacting surface (e.g., a delivery catheter or a patient's anatomy).

In some embodiments, a delivery sheath 712 and/or a delivery catheter at least partially within the delivery sheath 712 may have one or more spiral cuts in a surface thereof. Rotation of the delivery sheath 712 relative to the delivery catheter may engage the one or more spiral cuts and provide a further longitudinal force to translate the delivery sheath 712 in a longitudinal direction. For example, a pitch of the threaded surface of the first threaded member 752 and second threaded member 754 may be substantially the same as the pitch of the one or more spiral cuts in a surface of the delivery sheath 712 and/or delivery catheter such that at portion of the delivery sheath 712 may threadably engage with the delivery catheter.

Figure 16:
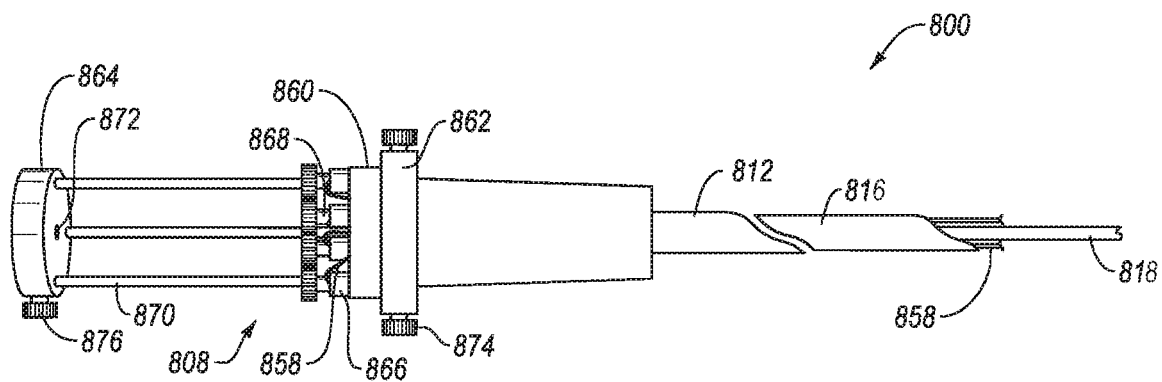
FIG. 16 is a side partial cutaway view of an embodiment of an elongated member and a proximal end cap, according to the present disclosure.
Figure 17:
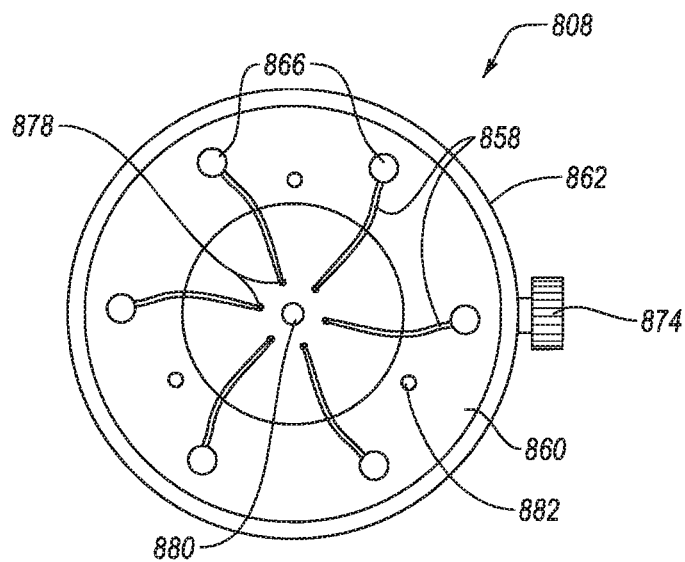
FIG. 17 is a proximal end view the embodiment of the proximal end cap of FIG. 16.

An intravascular device delivery system, as described in the present disclosure, may experience longitudinal forces on a delivery sheath of 40 pounds (177.9 Newtons) or more. A conventional delivery catheter may deflect when a delivery sheath around the delivery catheter transmits the longitudinal forces along a length thereof. In some embodiments, such as shown in FIGS. 16 and 17, an intravascular device delivery system 800 may include a handle 808 having a proximal end cap 860 configured to support one or more tension cables 858 in an inner catheter 816. The tension cables 858 may be used to selectively apply a tension force to one or more portions of the inner catheter 816 and may extend from the proximal end cap 860 through at least a portion of the longitudinal length of the inner catheter 816.

In some embodiments, the tension force applied by the tension cables 858 may allow the handle 808 to apply a substantially uniform tension force across the inner catheter 816, supporting the inner catheter 816 and resisting movement of the inner catheter 816 when moving the delivery sheath 812. For example, the tension force across the inner catheter may cause one or more coils to compress within one or more elements in the intravascular device delivery system 800 to stack the coils. Stacking the coils prior to moving one or more elements of the intravascular device delivery system 800 relative to one another may limit or prevent undesired or unintended movement of an element. In other embodiments, the tension force applied by the tension cables 858 may generate a torque on the inner catheter 816 to deflect at least a portion of the inner catheter 816 in a lateral direction.

In some embodiments, the proximal end cap 860 may be proximal to a housing 862 that is connected to the inner catheter 816. In some embodiments, the handle 808 may include a guidewire cap 864 located proximally of the proximal end cap 860.

The proximal end cap 860 may have a one or more tensioners 866 thereon that are rotatable relative to the proximal end cap 860. In some embodiments, at least one tensioner 866 may have a connection point 868 thereon or therethrough to which a tension cable 858 may connect. For example, the connection point 868 may be an aperture through the tensioner 866. A portion of a tension cable 858 may insert through the aperture and be bound around the tensioner 866. The tensioner 866 may be rotated after a tension cable 858 is connected to a connection point 868 and the tension cable 858 may be urged in a proximal direction. In other embodiments, the tensioner 866 and tension cable 858 may be replaced by a hypotube, such as a laser cut hypotube.

In some embodiments, the tensioner 866 may limit and/or prevent movement of a tension cable 858 attached thereto up to a break force of the tension cables 858. For example, the tension cables 858 may be made of or include steel, tungsten, organic filaments, inorganic filaments, polymers, glasses, ceramics, or combinations thereof. In some embodiments, the break force of the tension cables 858 may be in a range having an upper value, a lower value, or upper and lower values including any of 8 pounds, 10 pounds, 15 pounds, 20 pounds, 22 pounds, 24 pounds, 26 pounds, 28 pounds, 30 pounds, 35 pounds, 40 pounds, 45 pounds, 50 pounds or any values therebetween. For example, the break force of the tension cables 858 may be in a range of 8 pounds to 50 pounds. In other examples, the break force of the tension cables 858 may be in a range of 15 pounds to 35 pounds. In yet other examples, the break force of the tension cables 858 may be in a range of 20 pounds to 30 pounds.

The guidewire cap 864 may be longitudinally slidable relative to the proximal end cap 860 along the one or more rails 870. The guidewire cap 864 may include a guidewire connection 872 located thereon or therein. In some embodiments, a guidewire may be connected the guidewire cap 864 and directed through at least a portion of an inner catheter 816. In other embodiments, the guidewire cap 864 may be stationary and a guidewire lumen may be positioned within the guidewire connection 872. In at least one embodiment, the guidewire lumen may be selectively fixed to the guidewire connection 872, such as by a set screw, a thumb screw, a clip, a clamp, a tab, a pin, other mechanical locking feature, or combinations thereof. To limit and/or prevent collapse of the guidewire lumen when pinched down with a set screw or similar fastener in the guidewire connection 872, the guidewire lumen may be reinforced, such as with a metallic hypotube. In some embodiments, a guidewire lumen may be at least partially longitudinally elastic. The longitudinal elasticity of the guidewire lumen may allow the guidewire lumen to be placed under tension and longitudinally fixed at the guidewire connection 872. The elasticity of the guidewire lumen may thereby apply a tension force to a distal end of the guidewire lumen even during movement of one or more elements of the elongated member. A guidewire may be positioned in the guidewire lumen and longitudinally slidable relative to the guidewire lumen.

In some embodiments, the proximal end cap 860, housing 862, and guidewire cap 864 may be longitudinally fixed relative to one another along the one or more rails 870. In other embodiments, the proximal end cap 860, housing 862, and guidewire cap 864 may be longitudinally slidable relative to one another along the one or more rails 870, as described herein. One or more of the proximal end cap 860, housing 862, and guidewire cap 864 may be selectively securable relative to the one or more rails 870 to limit or prevent longitudinal movement of the proximal end cap 860, housing 862, or guidewire cap 864 relative to at least one other of the proximal end cap 860, housing 862, and guidewire cap 864. For example, the proximal end cap 860 and the guidewire cap 864 may be longitudinally securable relative to the rails to allow the delivery sheath 812 to translate in a longitudinal direction relative to the inner catheter 816 and/or a guidewire 818 during use of the intravascular device delivery system 800.

In some embodiments, the housing 862 may include one or more housing fastening members 874 positioned and configured to limit or prevent longitudinal movement of the housing 862 relative to the one or more rails 870. For example, the one or more housing fastening members 874 may include a set screw, a thumb screw, a clip, a clamp, a tab, a pin, other mechanical locking feature, or combinations thereof that may engage with or interact with the at least one of the one or more rails 870. In at least one embodiment, a housing 862 may have at least one housing fastening member 874 for each of the one or more rails 870.

In some embodiments, the guidewire cap 864 may include one or more cap fastening members 876 positioned and configured to limit or prevent longitudinal movement of the guidewire cap 864 relative to the one or more rails 870. For example, the one or more cap fastening members 876 may include a set screw, a thumb screw, a clip, a clamp, a tab, a pin, other mechanical locking feature, or combinations thereof that may engage with or interact with the at least one of the one or more rails 870. In at least one embodiment, a guidewire cap 864 may have at least one cap fastening member 876 for each of the one or more rails 870.

FIG. 17 is an end view of the proximal end cap 860 and housing 862 with the guidewire cap 864 not shown and one or more rails 870 not shown. In some embodiments, the proximal end cap 860 may have one or more tensioners 866 positioned thereon. At least one tensioner 866 may selectively tension a tension cable 858 connected to the tensioner 866. The tension cable 858 may be located through a tension cable aperture 878 in the proximal end cap 860. In some embodiments, the proximal end cap 860 may have at least one tensioner 866 for each tension cable aperture 878. In some embodiments, the tension cable aperture 878 may be configured to allow the tension cable 858 to pass through the tension cable aperture 878 with little to no friction therebetween. For example, tension cable aperture 878 may be an aperture through a portion of the proximal end cap 860 made of or including PTFE or other material having a coefficient of friction less than about 0.15. In other embodiments, the tension cable aperture 878 may be an aperture through a portion of the proximal end cap 860 made of or including a metal such that the tension cable 858 does not cut through a portion of the tension cable aperture 878 and/or proximal end cap 860 while under tension. In other examples, the tension cable aperture 878 may be lined with a material to reduce friction between the tension cable 858 and the tension cable aperture 878 and/or proximal end cap 860.

In some embodiments, the proximal end cap 860 may have at least one tensioner 866 for each tension cable 858. In other embodiments, at least one tensioner 866 may apply a tension force to a plurality of tension cables 858. The tension cable 858 may pass through the walls of a delivery catheter and the tension cable aperture 878 to a tensioner 866. The proximal end cap 860 may have a central aperture 880 that may provide communication with a central lumen of the delivery catheter. The tensioners 866 may be positioned about the central aperture 880.

In some embodiments, the tensioners 866 may be spaced at equal angular intervals about the central aperture 880 on the proximal end cap 860. For example, FIG. 17 illustrates six tensioners 866 positioned at 60° intervals. In another example, three tensioners 866 may be positioned at 120° intervals. In other embodiments, the tensioners 866 may be positioned at irregular angular intervals. In yet other embodiments, the tensioners 866 may be spaced at alternating intervals about the proximal end cap 860. For example, six tensioners 866 may be spaced at alternating intervals of 40° and 80° to form three pairs of tensioners 866. Pairing tensioners 866 may provide increased tactile identification of the tensioners 866 during operation of the proximal end cap 860.

After a user applies a tension force to the one or more tension cables 858 to tension the intravascular device delivery system using the one or more tensioners 866, a user may move the delivery sheath to deploy and/or recapture an intravascular device as described herein. Tensioning all of tension cables 858 may limit the movement of the delivery catheter during movement of the delivery sheath relative to the delivery catheter. In other embodiments, the proximal end cap 860 may be moved longitudinally in a distal direction relative to the housing 862 to apply a tension force to any tension cables 858 that were not previously tensioned. The housing fastening member 874 may then secure the longitudinal position of the proximal end cap 860 relative to the housing 862. After securing the proximal end cap 860, a user may move the delivery sheath in a longitudinal direction either by translating or by translating and rotating the delivery sheath, as described in relation to FIG. 13 through FIG. 16.

Figure 18:
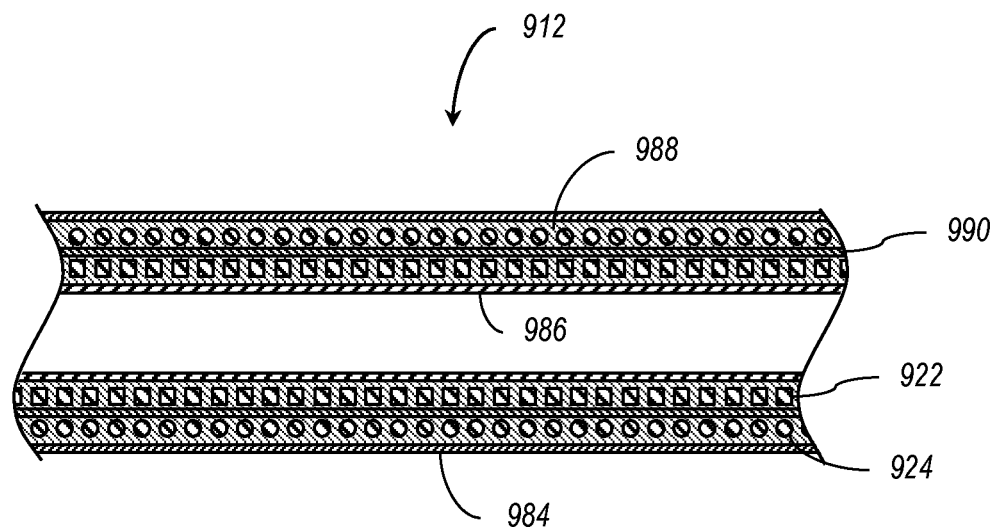
FIG. 18 illustrates a side cross-sectional view of an embodiment of a delivery sheath with tensioning elements within the wall of the delivery sheath.

FIG. 18 is a side cross-sectional view of an embodiment of a delivery sleeve 912 having at least one tensioning element to transmit tension force along a length thereof and/or steer the delivery sleeve 912. The delivery sleeve 912 may include an inner layer 922 and an outer layer 924. In some embodiments, the inner layer 922 and outer layer 924 each include or are a spiral coil. For example, the inner layer 922 is a coil with a rectangular transverse cross-section and the outer layer 924 is a coil with a round transverse cross-section. In other examples, the inner layer 922 and outer layer 924 may have similar transverse cross-sections. In yet other examples, the inner layer 922 may be a coil with a round transverse cross-section and the outer layer 924 may be a coil with a rectangular transverse cross-section.

In some embodiments, the inner layer 922 has a transverse thickness in a range having an upper value, a lower value, or upper and lower values including any of 0.001 inches, 0.002 inches, 0.003 inches, 0.004 inches, 0.005 inches, 0.006 inches, 0.007 inches, 0.008 inches, 0.009 inches, 0.010 inches, 0.012 inches, 0.014 inches, 0.016 inches, 0.018 inches, 0.020 inches, or any values therebetween. For example, the inner layer 922 may have a transverse thickness greater than 0.001 inches. In another example, the inner layer 922 may have a transverse thickness less than 0.020 inches. In yet another example, the inner layer 922 has a transverse thickness in range of 0.001 inches to 0.020 inches.

An inner layer 922 with a rectangular transverse cross-section may have a transverse cross-sectional width that is greater than a transverse cross-sectional height by a factor in a range having an upper value, a lower value, or upper and lower values including any of 1.1, 1.2, 1.4, 1.6, 1.8, 2.0, 2.5, 3.0, 3.5, 4.0, 4.5, 5.0, or any values therebetween. For example, the inner layer 922 may have a transverse cross-sectional width to height ratio greater than 1.1. In another example, the inner layer 922 may have a transverse cross-sectional width to height ratio less than 5.0. In yet another example, the inner layer 922 may have a transverse cross-sectional width to height ratio from 1.1 to 5.0.

In some embodiments, the outer layer 924 has a transverse thickness in a range having an upper value, a lower value, or upper and lower values including any of 0.001 inches, 0.002 inches, 0.003 inches, 0.004 inches, 0.005 inches, 0.006 inches, 0.007 inches, 0.008 inches, 0.009 inches, 0.010 inches, 0.012 inches, 0.014 inches, 0.016 inches, 0.018 inches, 0.020 inches, or any values therebetween. For example, the outer layer 924 may have a transverse thickness greater than 0.001 inches. In another example, the outer layer 924 may have a transverse thickness less than 0.020 inches. In yet another example, the outer layer 924 has a transverse thickness in range of 0.001 inches to 0.020 inches.

An outer layer 924 with a rectangular transverse cross-section may have a transverse cross-sectional width that is greater than a transverse cross-sectional height by a factor in a range having an upper value, a lower value, or upper and lower values including any of 1.1, 1.2, 1.4, 1.6, 1.8, 2.0, 2.5, 3.0, 3.5, 4.0, 4.5, 5.0, or any values therebetween. For example, the outer layer 924 may have a transverse cross-sectional width to height ratio greater than 1.1. In another example, the outer layer 924 may have a transverse cross-sectional width to height ratio less than 5.0. In yet another example, the outer layer 924 may have a transverse cross-sectional width to height ratio from 1.1 to 5.0.

In some embodiments, the delivery sleeve 912 includes an outer jacket 984. The outer jacket 984 may include or be made of PEBAX 25D to 75D, Nylon, polyethylene (PE), PET, TPU, fluorinated ethylene propylene, other similar materials, or combinations thereof. In some embodiments, the outer jacket 984 includes a lubricious material or combination of lubricious materials in the bulk material of the outer jacket 984. In other embodiments, the outer jacket 984 has a coating of lubricious material applied thereto. For example, the lubricious material may include silicone, PTFE or similar products, such as PFA, fluorinated ethylene propylene, other flouropolymer, ceramic coatings, one or more materials combined with a polymer structure (such as PROPELL available from FOSTER CO.), other materials, or combinations thereof. In yet other embodiments, the outer jacket 984 includes a hydrophobic and/or hydrophilic material to reduce friction.

In some embodiments, the delivery sleeve 912 includes an inner liner 986. The inner liner 986 may be or include a friction-reducing layer and/or coating. For example, the inner liner 986 may include a PTFE layer. In other examples, the inner liner 986 may include other lubricious coatings, such as (PFA), fluorinated ethylene propylene, other flouropolymer, ceramic coatings, one or more materials combined with a polymer structure (such as PROPELL available from FOSTER CO.), other materials, or combinations thereof. In yet other examples, the inner liner 986 may include or be a hydrophilic or hydrophobic layer.

To provide flexibility, the inner liner 986 may have a transverse thickness of between 0.001 inches and 0.050 inches. In some embodiments, the transverse thickness is between 0.010 inches and 0.040 inches. In other embodiments, the transverse thickness is between 0.020 inches and 0.030 inches. In at least one embodiment, the transverse thickness is about 0.025 inches.

In some embodiments, the inner liner 986 may have one or more relief features. For example, the inner liner 986 may be cut to enhance flexibility. In at least one embodiment, the inner liner 986 may be spiral cut along at least a portion of the longitudinal length thereof to increase flexibility of the inner liner 986. In some embodiments, the inner liner 986 may further be stretched in the longitudinal direction such that the cuts are open at a neutral position, such that during bending of the delivery sleeve 912 the cuts on the inside of the curve may close freely with reduced resistance to compression.

In some embodiments, both the inner layer 922 and outer layer 924 may be encapsulated in a body 988. In other embodiments, the outer layer 924 may be radially outside the body 988, allowing the outer layer 924 to displace relative to the body 988 during steering of the delivery sleeve 912 in the patient's body. In yet other embodiments, the outer layer 924 may be longitudinally moveable relative to the body 988. For example, the outer layer 924 may be retractable in a proximal direction to allow a distal portion of the body 988 and inner layer 922 to be more flexible than the delivery sleeve 912 with the outer layer 924 present. The outer layer 924 may then be configured to advance over the body 988 in the distal direction and abut a distal end cap of the delivery sleeve 912 when additional compressive force is needed in the distal direction.

In some embodiments, the delivery sleeve 912 has a body 988 with at least one tensioning element 990 extending in a longitudinal direction therethrough and affixed to an end cap at the distal end of the delivery sleeve 912. In some embodiments, the tensioning element 990 may transmit a force (tension and/or compression) along the length of the delivery sleeve 912. In some embodiments, the tension element 990 may be used to steer (e.g., bend or change directions of) the delivery sleeve 912 or a portion thereof (e.g., a distal end). In some embodiments, a tensioning element 990 may be positioned between the inner layer 922 and the outer layer 924. In other examples, a tensioning element 990 may be positioned radially outside the inner layer 922 and the outer layer 924. In yet other examples, a tensioning element 990 may be positioned radially inside the inner layer 922 and the outer layer 924. In further examples, a delivery sleeve may have a plurality of tensioning elements 990 positioned in a combination of the locations described.

In some embodiments, the tensioning element 990 may include or be made of steel, tungsten, organic filaments, inorganic filaments, polymers, glasses, ceramics, or combinations thereof. In some embodiments, the break force of the tensioning element 990 may be in a range having an upper value, a lower value, or upper and lower values including any of 8 pounds, 10 pounds, 15 pounds, 20 pounds, 22 pounds, 24 pounds, 26 pounds, 28 pounds, 30 pounds, 35 pounds, 40 pounds, 45 pounds, 50 pounds, 55 pounds, 60 pounds, 65 pounds, 70 pounds, 75 pounds, 80 pounds, 85 pounds, 90 pounds, 95 pounds, 100 pounds, or any values therebetween. For example, the break force of the tensioning element 990 may be in a range of 8 pounds to 100 pounds. In other examples, the break force of the tensioning element 990 may be in a range of 15 pounds to 75 pounds. In yet other examples, the break force of the tensioning element 990 may be in a range of 20 pounds to 50 pounds.

In some embodiments, the tensioning element 990 has a transverse thickness in a range having an upper value, a lower value, or upper and lower values including any of 0.005 inches, 0.006 inches, 0.007 inches, 0.008 inches, 0.009 inches, 0.010 inches, 0.012 inches, 0.014 inches, 0.016 inches, 0.018 inches, 0.020 inches, 0.022 inches, 0.024 inches, 0.026 inches, 0.028 inches, 0.030 inches, or any values therebetween. For example, the tensioning element 990 may have a transverse thickness greater than 0.005 inches. In another example, the tensioning element 990 may have a transverse thickness less than 0.030 inches. In yet another example, the tensioning element 990 has a transverse thickness in range of 0.005 inches to 0.030 inches.

Figure 19:
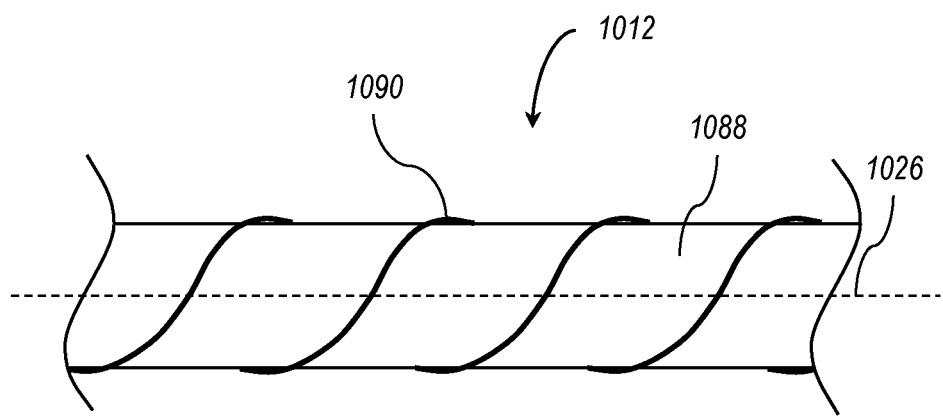
FIG. 19 illustrates a side view of an embodiment of a delivery sheath with a spiral tensioning element therein.

FIG. 19 illustrates another embodiment of a delivery sleeve 1012 with at least one tensioning element 1090. In some embodiments, the tensioning element 1090 is oriented at an angle to a longitudinal axis 1026 to provide greater flexibility by spiraling about the body 1088. The tensioning element 1090 may be oriented at an angle to the longitudinal axis in a range having an upper value, a lower value, or upper and lower values including any of 1°, 5°, 10°, 15°, 20°, 25°, 30°, 35°, 40°, 45°, 50°, 55°, 60°, or any values therebetween. For example, the tensioning element 1090 may be oriented at an angle to the longitudinal axis greater than 1°. In other examples, the tensioning element 1090 may be oriented at an angle to the longitudinal axis less than 60°. In yet other examples, the tensioning element 1090 may be oriented at an angle between 1° and 60°. In further examples, the tensioning element 1090 may be oriented at an angle between 30° and 45°.

In some embodiments, the delivery sleeve 1012 may have a plurality of tensioning elements 1090. FIG. 19 illustrates a plurality of tensioning elements 1090 helixed together and about the body 1088. Upon deflection of the body delivery sleeve 1012, each tensioning element 1090 is deflected substantially equally with respect to the other tensioning elements 1090. Equal deflection allows the tensioning elements to experience the same lengthening or shortening relative to the body 1088 during deflection, reducing any steering bias under deflection due to a plurality of tensioning elements 1090.

An intravascular device delivery system having a delivery sheath and/or a handle according to the present disclosure may allow application and transmission of greater longitudinal forces than a conventional intravascular device delivery system from the proximal end of an elongated member to a distal end of the elongated member to deploy an intravascular device, while maintaining flexibility and accuracy of a steerable delivery catheter.

In light of the disclosure herein, an embodiment of an intravascular device delivery system can include an elongated element having a longitudinal axis along a length thereof. The elongated element may have a body with an outer surface and an inner surface. The body may have a continuous spine extending in a direction of the longitudinal axis and a plurality of cuts from the outer surface to the inner surface.

In some embodiments, the plurality of cuts include a first ring at a first longitudinal position including an island cut, and a second ring at a second longitudinal position including a slit cut. In some embodiments, at least part of the slit cut and at least part of the island cut rotationally overlap. In some embodiments, an island cut percentage of a thickness in the direction of the longitudinal axis relative to a circumference of the body is between 0.20% and 0.45%.

In some embodiments, the continuous spine of the elongated element has a tensile strength of 40 pounds (177.9 Newtons) or greater. Similarly, in some embodiments, the continuous spine has a spine width percentage in a range of 0.40% to 0.90%. In some embodiments, the elongated element includes a plurality of rings perpendicular to the longitudinal axis, at least one of the plurality of rings having a ring length percentage relative to a circumference of the body between 0.60% and 1.30%. Further embodiments include a link between cuts, the link having a link width relative to a circumference of the body between 0.60% and 1.30%.

In light of the disclosure herein, an intravascular device delivery system includes an elongated member having a deliver catheter and a delivery sheath. The delivery catheter can have a proximal end, a distal end, and a longitudinal axis extending therebetween. The delivery sheath can be positioned radially outside and circumferentially about the delivery catheter and coaxial with the delivery catheter. The delivery sheath can include a body with an outer surface and an inner surface and a longitudinal axis extending along a length thereof. The body can have a continuous spine extending in a direction of the longitudinal axis and a plurality of cuts from the outer surface to the inner surface. In some embodiments, the intravascular device delivery system includes a wire braid circumferentially about the body of the delivery sheath. In some further embodiments, the intravascular delivery system also includes a friction-reducing layer located between at least part of the delivery sheath and the delivery catheter.

In some embodiments, the intravascular device delivery system also includes a handle connected to the elongated member at the proximal end of the elongated member. The handle can be configured to translate the delivery sheath longitudinally relative to the delivery catheter. In some cases, the handle is configured to rotate the delivery sheath about the longitudinal axis during longitudinal translation of the delivery sheath relative to the delivery catheter.

In some embodiments, the delivery sheath is moveable in a longitudinal direction relative to the delivery catheter. Similarly, in some embodiments the delivery sheath is rotatable about the longitudinal axis relative to the delivery catheter. Further, in some embodiments, at least a portion of the delivery sheath is translatable distally beyond the distal end of the delivery catheter.

In light of the disclosure herein, a method of delivering a medical device can include inserting an intravascular device delivery system including a delivery sheath having a continuous spine into a bodily lumen. The method can also include applying a distal longitudinal force to the delivery sheath and transmitting the distal force through the continuous spine and across one or more slit cuts of the delivery sheath. Further, the method can include applying a proximal longitudinal force to the delivery sheath and transmitting the proximal longitudinal force through the continuous spine of the delivery sheath. In some embodiments, the method also includes steering the delivery sheath with a steerable delivery catheter positioned radially within the delivery sheath.

In some embodiments, applying a proximal longitudinal force to the delivery sheath moves the delivery sheath longitudinally relative to the steerable delivery catheter. Similarly, in some embodiments applying a distal longitudinal force to the delivery sheath moves the delivery sheath longitudinally relative to a steerable delivery catheter.

In light of the disclosure herein, a hybrid tubular member can include an inner layer, an outer layer, and one or more tensioning elements. The inner layer may have a proximal end and a distal end, with a longitudinal axis extending therebetween. In some cases, the inner layer includes a coil. The outer layer may longitudinally overlap the inner layer and may be position circumferentially outside and around the inner layer. In some cases, the outer layer includes a coil. The one or more tensioning elements extend from the proximal end of the inner layer to the distal end of the inner layer.

In some embodiments, the inner layer has a rectangular transverse cross-section. Similarly, in some embodiments the outer layer has a rectangular transverse cross-section.

In some embodiments, at least one of the one or more tensioning elements has a break force of at least 50 pounds. In some embodiments, at least one of the one or more tensioning elements is angled relative to the longitudinal axis between 1° and 60°. In some embodiments, at least one of the one or more tensioning elements is positioned radially between the inner layer and the outer layer.

In some embodiments, the hybrid tubular member also includes a body encapsulating at least the inner layer. In some embodiments, the hybrid tubular member also includes an inner liner and/or an outer jacket.

The articles "a," "an," and "the" are intended to mean that there are one or more of the elements in the associated descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A hybrid tubular member, the tubular member comprising:
   a coil inner layer having a proximal end and a distal end, a longitudinal axis extending therebetween, an angle of the coil in relation to the longitudinal axis forming an inner layer angle; and
   a hypotube, with a plurality of openings, forming an outer layer longitudinally overlapping the inner layer and positioned circumferentially outside and adjacent to the inner layer, the outer layer including one or more constituent elements having an outer layer angle relative to the longitudinal axis that is less than the inner layer angle; and a braided contact layer disposed within the coil inner layer, the braided contact layer forming a lumen to receive an intravascular device, an inner surface of the braided contact layer being more continuous than a surface of the coil inner layer.

2. The tubular member of claim 1, wherein the inner layer has an outer diameter and the outer layer has an inner diameter, and the outer diameter of the inner layer is substantially equal to the inner diameter of the outer layer.

3. The tubular member of claim 1, wherein the inner layer has an outer diameter and the outer layer has an inner diameter, and the outer diameter of the inner layer is less than the inner diameter of the outer layer such that a gap is formed therebetween.

4. The tubular member of claim 1, wherein the inner layer and outer layer are longitudinally fixed relative one another at a proximal end and a distal end of the inner layer.

5. The tubular member of claim 1, wherein the inner layer angle and outer layer angle define a layer angle ratio between 1.1 and 5.0.

6. The tubular member of claim 1, further comprising one or more tensioning elements.

7. The tubular member of claim 6, wherein the one or more tensioning elements extend from the proximal end of the inner layer to the distal end of the inner layer.

8. An intravascular device delivery system, the system comprising:
an elongated member, the elongated member including:
a delivery catheter having a proximal end, a distal end, and a longitudinal axis extending therebetween;
a hybrid delivery sheath positioned radially outside and circumferentially about the delivery catheter and coaxial with the delivery catheter, the hybrid delivery sheath including:
a coil inner layer having a proximal end and a distal end, a longitudinal axis extending therebetween, an angle of the coil in relation to the longitudinal axis forming an inner layer angle; and
a hypotube, with a plurality of openings, forming an outer layer longitudinally overlapping the inner layer and positioned circumferentially outside and around the inner layer, the outer layer including one or more constituent elements having an outer layer angle relative to the longitudinal axis that is less than the inner layer angle; and a braided contact layer disposed within the coil inner layer, the braided contact layer forming a lumen to receive an intravascular device, an inner surface of the braided contact layer being more continuous than a surface of the coil inner layer.

9. The system of claim 8, wherein the hybrid delivery sheath is moveable in a longitudinal direction relative to the delivery catheter.

10. The system of claim 8, wherein the hybrid delivery sheath is rotatable about the longitudinal axis relative to the delivery catheter.

11. The system of claim 8, wherein the hybrid delivery sheath is movable in at least two directions and relative to the delivery catheter.

12. The system of claim 8, wherein the outer layer and the coil inner layer are movable in at least two directions and relative to one another.

13. The system of claim 8, wherein at least one of the coil inner layer and the outer layer is movable in at least two directions and relative to the delivery catheter.

14. The system of claim 8, further comprising a handle connected to the elongated member at the proximal end of the elongated member, the handle configured to translate the hybrid delivery sheath longitudinally relative to the delivery catheter.

15. The system of claim 14, wherein the handle is configured to rotate the hybrid delivery sheath about the longitudinal axis during longitudinal translation of the hybrid delivery sheath relative to the delivery catheter.

16. The system of claim 8, wherein at least a portion of the hybrid delivery sheath is translatable distally beyond the distal end of the delivery catheter.

17. The system of claim 8, further comprising a friction-reducing layer located between at least part of the hybrid delivery sheath and the delivery catheter.

* * * * *